(12) United States Patent
Kawanishi et al.

(10) Patent No.: US 12,406,373 B2
(45) Date of Patent: Sep. 2, 2025

(54) CONTROL APPARATUS, CONTROL METHOD, RADIATION IMAGING SYSTEM, AND STORAGE MEDIUM

(71) Applicant: CANON KABUSHIKI KAISHA, Tokyo (JP)

(72) Inventors: Tomohiro Kawanishi, Tokyo (JP); Hironori Yamashita, Kanagawa (JP); Masaya Kawai, Kanagawa (JP); Keiko Uehara, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 413 days.

(21) Appl. No.: 17/818,505

(22) Filed: Aug. 9, 2022

(65) Prior Publication Data
US 2023/0047620 A1 Feb. 16, 2023

(30) Foreign Application Priority Data

Aug. 16, 2021 (JP) .................. 2021-132310

(51) Int. Cl.
G06T 7/00 (2017.01)
G06T 7/80 (2017.01)
(52) U.S. Cl.
CPC .............. G06T 7/0016 (2013.01); G06T 7/80 (2017.01); G06T 2207/30204 (2013.01)
(58) Field of Classification Search
CPC .................... A61B 6/54; A61B 6/547
See application file for complete search history.

(56) References Cited

U.S. PATENT DOCUMENTS

| 2006/0116566 A1* | 6/2006 | Bruijns | ..................... A61B 6/00 600/407 |
| 2008/0130837 A1* | 6/2008 | Heath | ..................... A61B 6/587 378/205 |
| 2011/0075817 A1* | 3/2011 | Takahashi | ............ A61B 6/4283 378/189 |
| 2011/0311026 A1* | 12/2011 | Lalena | ................... G16H 40/63 378/98.5 |
| 2014/0072105 A1* | 3/2014 | Belei | ...................... A61B 6/461 378/205 |
| 2015/0010129 A1* | 1/2015 | Schliermann | ........ G01N 23/043 378/91 |

FOREIGN PATENT DOCUMENTS

| JP | 2020162971 A | 10/2020 |
| JP | 2021115074 A | 8/2021 |
| WO | 2020036225 A1 | 2/2020 |

* cited by examiner

Primary Examiner — Wen W Huang
(74) Attorney, Agent, or Firm — Canon U.S.A., Inc. IP Division

(57) ABSTRACT

An apparatus includes an acquisition unit and a display control unit. The acquisition unit is configured to acquire information about an orientation of a detector. The detector is configured to capture a radiation image by detecting radiation, and includes a plurality of receptor fields for performing automatic exposure control and a mark enabling identification of the orientation of the detector. The display control unit is configured to display an icon related to the detector on a display unit based on the acquired information about the orientation of the detector.

23 Claims, 14 Drawing Sheets

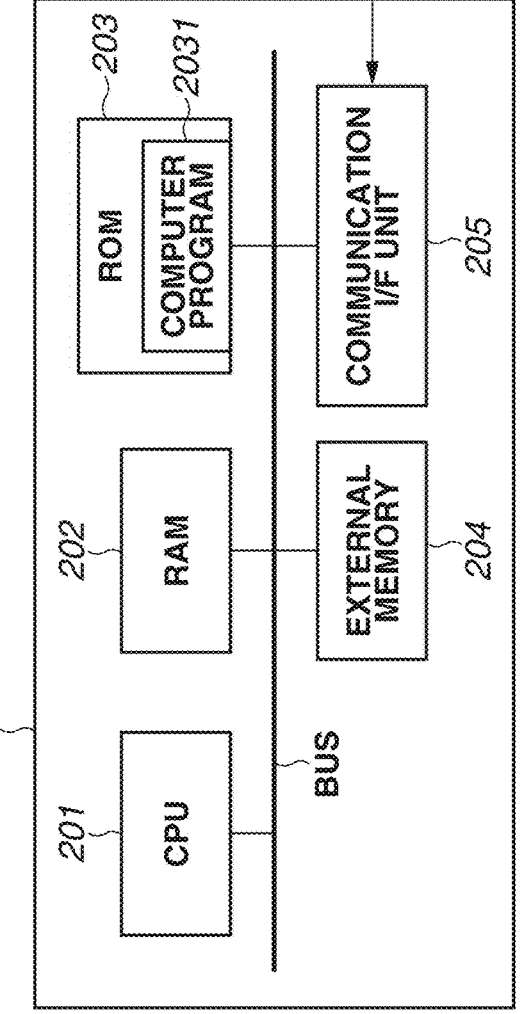
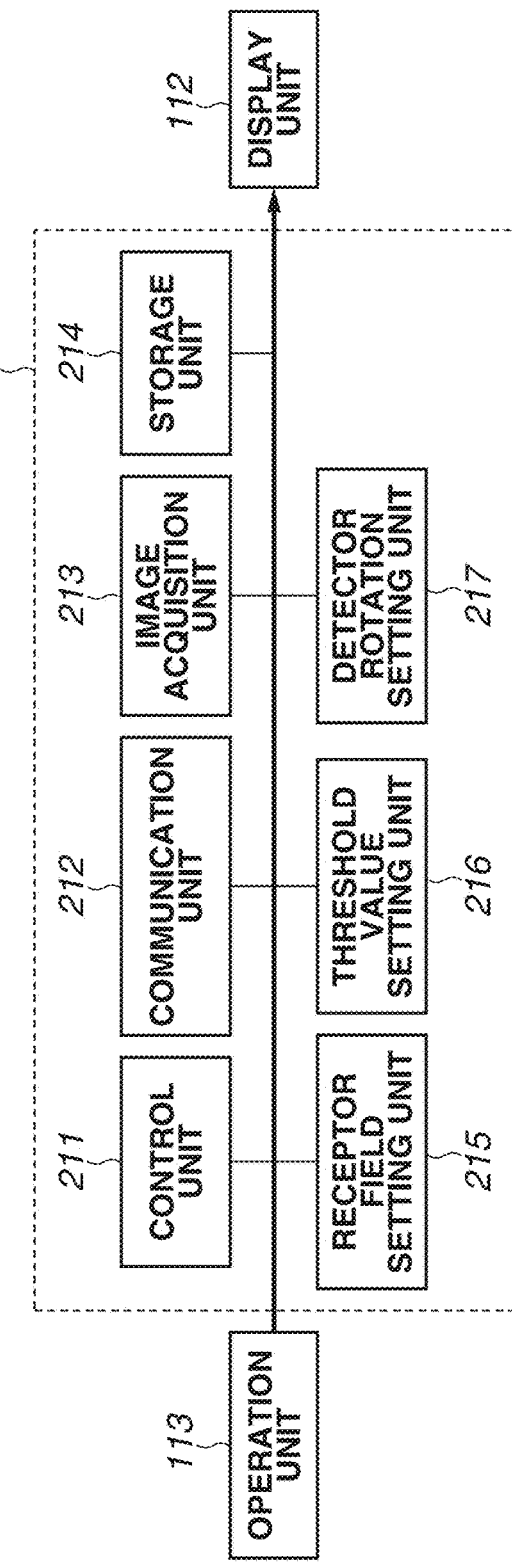

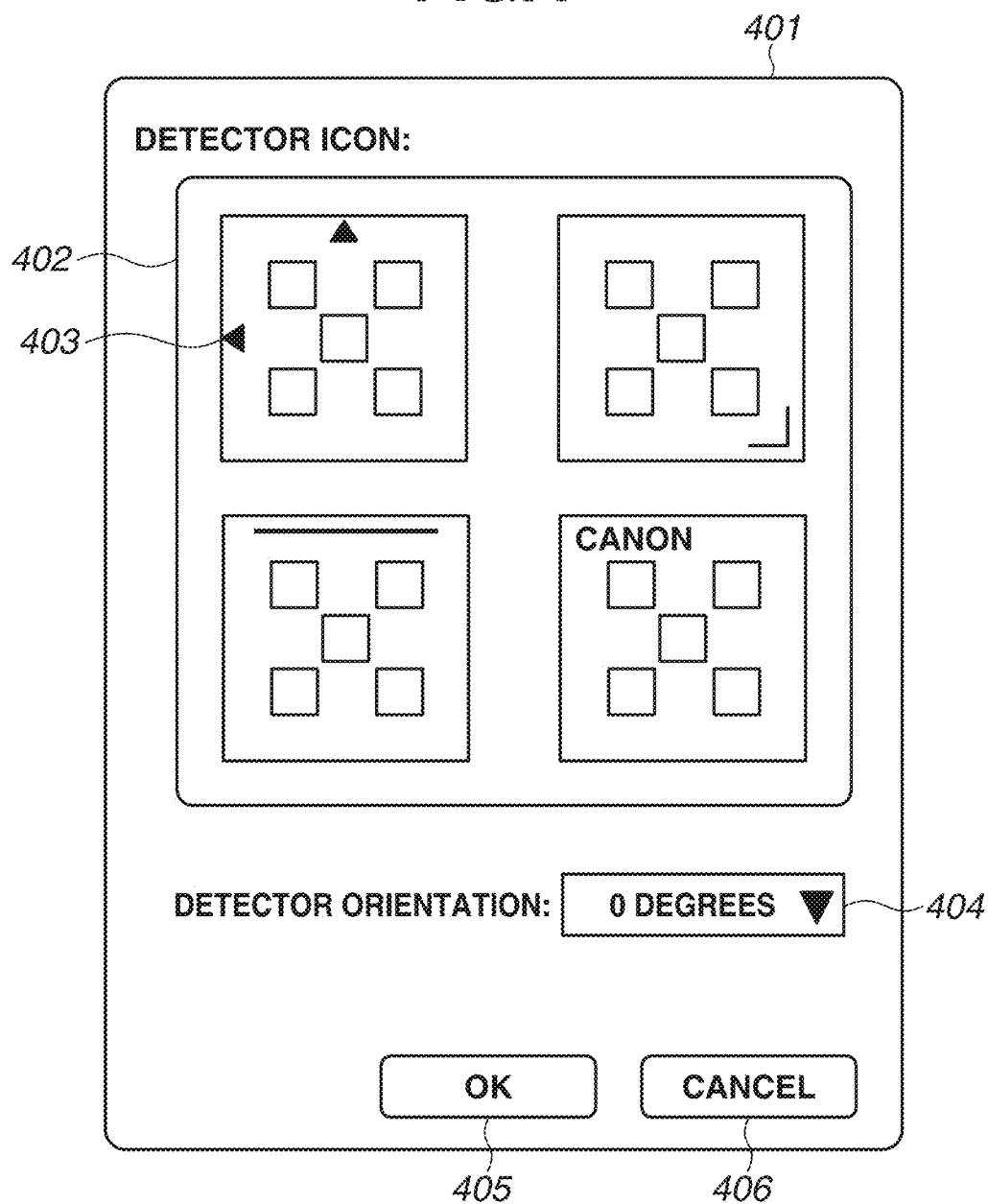

CONTROL APPARATUS, CONTROL METHOD, RADIATION IMAGING SYSTEM, AND STORAGE MEDIUM

BACKGROUND

Technical Field

The aspect of the embodiments relates to a control apparatus that performs automatic exposure control, a control method, a radiation imaging system, and a storage medium.

Description of the Related Art

In recent years, the multi-functionalization of radiation imaging apparatuses that detect radiation such as X-ray and are used in the medical field has been discussed. As one example thereof, the incorporation of a radiation irradiation monitoring function into the radiation imaging apparatuses has been discussed.

This function makes it possible to, for example, detect the timing at which irradiation with radiation from a radiation source is started, detect the timing at which the irradiation with the radiation is to be stopped, and detect the radiation irradiation amount or the cumulative irradiation amount.

The function makes it also possible to perform automatic exposure control (AEC) by detecting the cumulative irradiation amount of radiation transmitted through a subject and stopping the irradiation with the radiation from the radiation source at the time when the detected cumulative irradiation amount reaches an appropriate amount.

Generally, in a case where the automatic exposure control is performed using a flat panel detector (FPD) as such a radiation imaging apparatus, a plate-like AEC detector, which is provided as a different apparatus from the FPD, is disposed to be sandwiched between the subject and the FPD.

The AEC detector measures a radiation dose transmitted through the subject, in one or a plurality of preselected radiation detection areas (receptor fields) for measuring radiation, and controls the stop of the X-ray irradiation when the measured dose reaches a predetermined dose.

In the case of imaging using the AEC detector as the different detector, due to difficulty of carrying the FPD and the AEC detector, imaging with stationary installation where the radiation imaging apparatus is installed on a stand in a limited imaging room, such as erect imaging or decubitus imaging, is generally performed.

On the other hand, the use of a built-in AEC function in the radiation imaging apparatus makes the radiation imaging apparatus detachable from the stand and portable, thereby enabling AEC imaging with the subject in a posture other than standing and lying positions and without using a limited imaging room. However, in a case where the radiation imaging apparatus is, for example, rotated with respect to the subject, when an operator is to identify the positions of the receptor fields to be used in the AEC imaging, it may be difficult to identify the positional relationship between the subject and the plurality of receptor fields compared to the case where the radiation imaging apparatus is installed on the stand.

For this reason, there is a possibility that the positions of the receptor fields selected in advance may be different from the positions expected by the operator, and this may cause a failure to perform appropriate exposure control and result in not acquiring a radiation image with an appropriate density.

For example, according to a method discussed in Japanese Patent Application Laid Open No. 2020-162971, an upper limit on usable receptor fields is changed in a case where a radiation imaging apparatus is detached from a stand.

However, with the method discussed in Japanese Patent Application Laid Open No. 2020-162971, it is difficult for the operator to identify the positions of the receptor fields in some cases.

SUMMARY

According to an aspect of the embodiments, an apparatus includes an acquisition unit configured to acquire information about an orientation of a detector, the detector being configured to capture a radiation image by detecting radiation, the detector including a plurality of receptor fields for performing automatic exposure control and a mark enabling identification of the orientation of the detector, and a display control unit configured to display an icon related to the detector on a display unit based on the acquired information about the orientation of the detector.

Further features of the disclosure will become apparent from the following description of exemplary embodiments with reference to the attached drawings.

BRIEF DESCRIPTION I/F THE DRAWINGS

FIGS. 2A and 2B are block diagrams illustrating a hardware configuration and a software configuration of a control apparatus, respectively.

FIG. 4 is a diagram illustrating an example of how a radiation detector display form and rotation information about the radiation detector are set.

DESCRIPTION I/F THE EMBODIMENTS

Exemplary embodiments of the disclosure will be described below with reference to the attached drawings.

Figure 1:
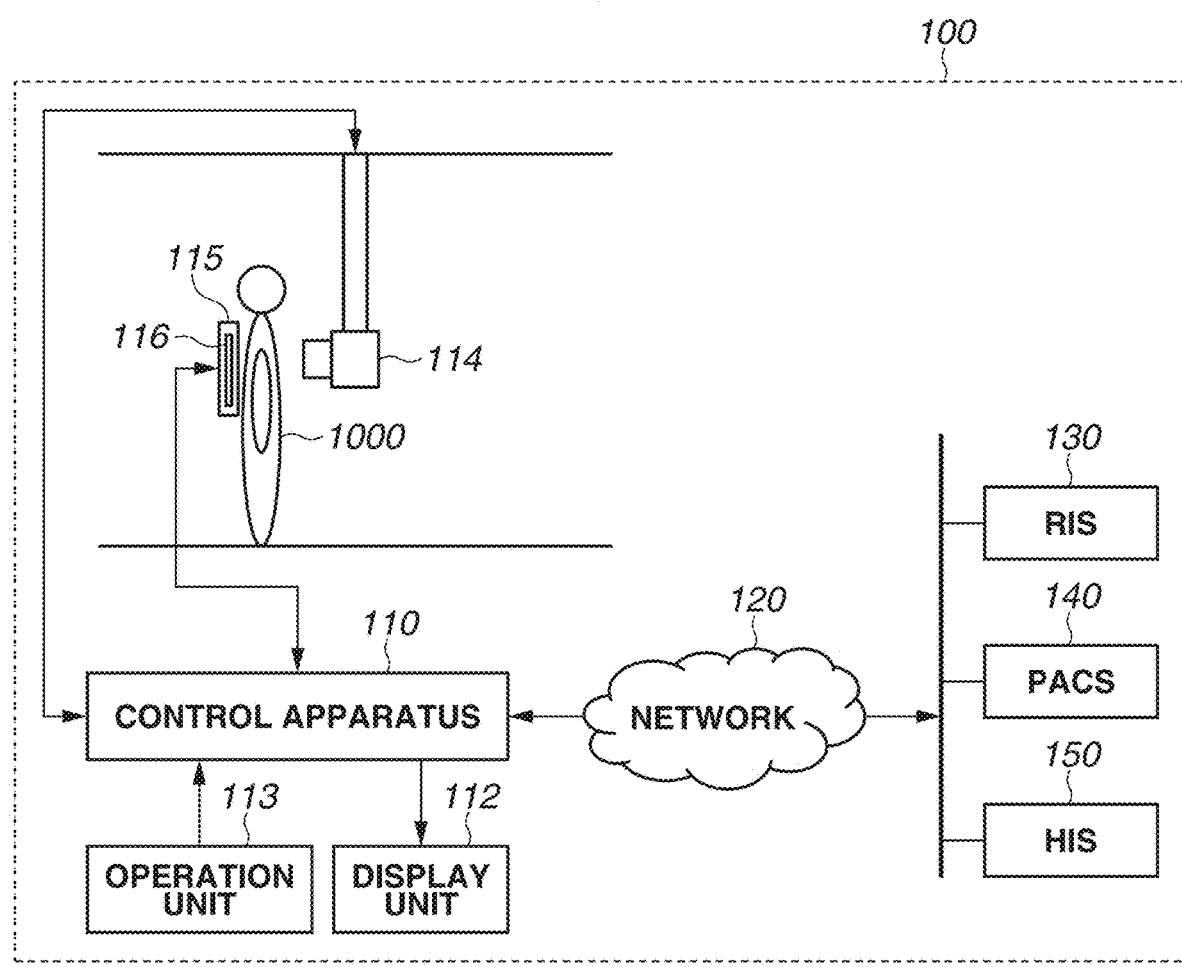
FIG. 1 is a diagram illustrating a schematic configuration of a radiation imaging system.

FIG. 1 schematically illustrates an example of a configuration of a radiation imaging system 100 according to a first exemplary embodiment of the disclosure. The radiation imaging system 100 includes a control apparatus 110, a radiation generation unit 114, a radiation detector 115, Radiology Information Systems (RIS) 130, Picture Archiving and Communication Systems (PACS) 140, and Hospital Information Systems (HIS) 150. The RIS 130 are information systems used in the department of radiology. The PACS 140 are systems including an image server. The HIS 150 are information systems used in hospitals.

The control apparatus (an imaging control apparatus) 110 is connected to a display unit 112, an operation unit 113, and the radiation generation unit 114 in a wired manner and is connected to the radiation detector 115 via wired communication or wireless communication. The control apparatus 110 communicates with these devices to control operations thereof. The wired communication can be performed via a local area network (LAN) such as Ethernet®, but may be performed using another wired communication method. The control apparatus (the imaging control apparatus) 110 may be wirelessly connected to the display unit 112, the operation unit 113, and the radiation generation unit 114.

The wireless communication is implemented by, for example, an antenna and a circuit board including a communication integrated circuit (IC). The circuit board including the communication IC performs communication processing according to a wireless LAN protocol via the antenna. A frequency band, a standard, and a method used in the wireless communication are not particularly limited. The control apparatus 110 may use proximity wireless communication such as near-field communication (NFC) or Bluetooth®, or a method such as Ultra Wide Band (UWB). The control apparatus 110 may support a plurality of wireless communication methods and select one of the methods to perform communication.

The control apparatus 110 is connected to the RIS 130, the PACS 140, and the HIS 150 via a network 120, and can exchange radiation images, patient information, and the like therewith.

The display unit 112 displays imaging examination information, captured radiation images, and various kinds of information. The operation unit 113 receives information input from an operator. In the present exemplary embodiment, the display unit 112 is a monitor (e.g., a liquid crystal display) and the operation unit 113 is a keyboard, a pointing device (e.g., a mouse), or a touch panel.

The radiation generation unit (a radiation generation apparatus) 114 includes a radiation tube that generates radiation, and irradiates a patient 1000, serving as a subject, with the radiation.

In the present exemplary embodiment, an example in which the radiation generation unit 114 is installed in a room where radiation imaging is performed, and a locational range where each radiation generation unit 114 performs irradiation with radiation is limited to a predetermined range is described as illustrated in FIG. 1, but a portable apparatus may be used as the radiation generation unit 114.

The radiation detector (a radiation imaging apparatus) 115 generates an image based on the radiation with which the patient 1000 is irradiated by the radiation generation unit 114.

Figure 3A:
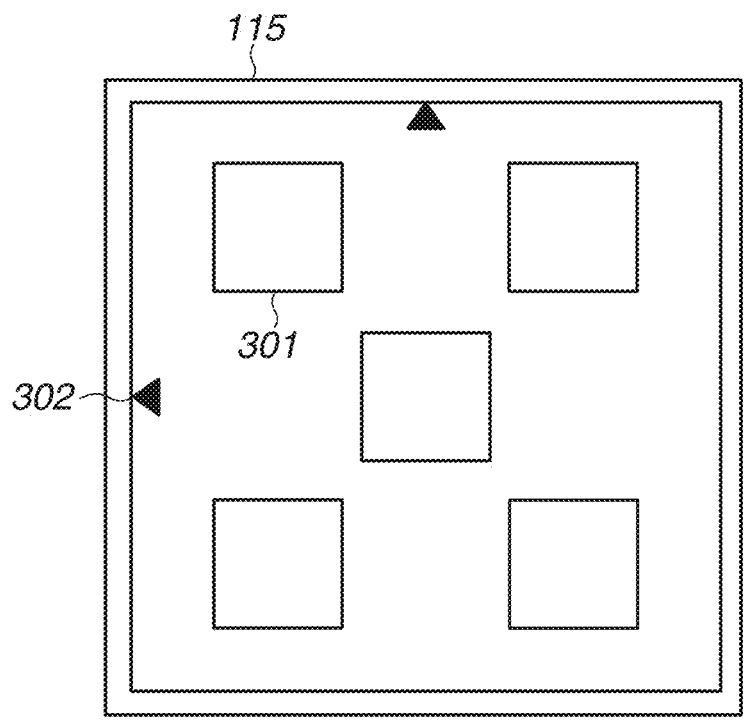
FIGS. 3A and 3B are diagrams each illustrating an example of arrangement of receptor fields built in a radiation detector.
Figure 3B:
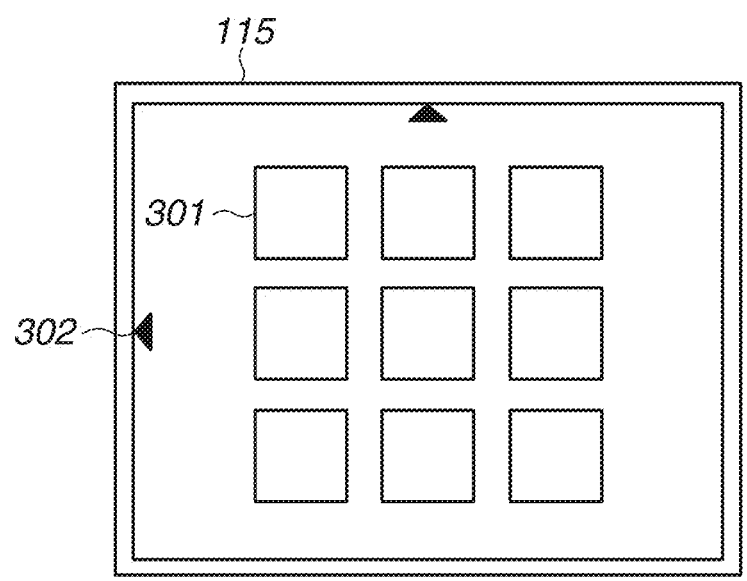

An automatic exposure control (AEC) function 116, which performs automatic exposure control, is built in the radiation detector 115, and one or a plurality of radiation detection areas (receptor fields) 301 for measuring radiation is arranged in the radiation detector 115 as illustrated in FIG. 3A or 3B.

The radiation detector 115 measures a radiation dose transmitted through the subject, in one or a plurality of receptor fields selected in advance from among the receptor fields 301, and controls the stop of the irradiation with the radiation when the measured dose reaches a predetermined dose.

The radiation detector 115 further includes a mark 302 (refer to FIGS. 3A and 3B) indicating a reference orientation so that the position(s) of the selected receptor field(s) can be easily identified. The mark 302 enables at least one side near the mark 302, among four sides forming a front surface of the radiation detector 115 on which the radiation is incident, to be used as the reference, thereby enabling the operator to easily identify the orientation of the radiation detector 115 based on the reference. While the example in which the radiation detector 115 is rectangular has been described above, the shape of the radiation detector 115 is not limited thereto. In addition, the mark 302 may be provided in a different manner as long as the mark 302 enables the operator to identify the orientation of the radiation detector 115.

The control apparatus 110 communicates with the radiation detector 115 to receive a radiation image and perform operation control, and performs image processing on radiation image data acquired by the radiation detector 115 detecting radiation and displays the processed data on the display unit 112 as a radiation image.

The radiation detector 115 is installed in a room or on a desk based on the locational range where the radiation generation unit 114 performs irradiation with radiation.

While the radiation imaging system 100 according to the present exemplary embodiment is described to include the RIS 130, the PACS 140, and the HIS 150, the radiation imaging system 100 may be configured not to include at least a part of the RIS 130, the PACS 140, and the HIS 150.

While FIG. 1 illustrates the example in which the radiation generation unit 114 and the radiation detector 115 are present as a radiation generation unit and a radiation detector, a combination of a radiation generation unit and a radiation detector is not limited thereto. For example, an additional combination of a radiation generation unit and a radiation detector may be included in the radiation imaging system 100.

Next, an example of a configuration of the control apparatus 110 according to the present exemplary embodiment will be described. FIG. 2A schematically illustrates an example of a hardware configuration of the control apparatus 110. The control apparatus 110 includes a central processing unit (CPU) 201, a random access memory (RAM) 202, a read only memory (ROM) 203, an external memory 204, and a communication interface (I/F) unit 205, and these components are connected to each other via a bus.

The CPU 201 comprehensively controls the operation of the control apparatus 110, and controls each of the components illustrated in FIG. 2A (i.e., the RAM 202 to the communication I/F unit 205) via the bus.

The RAM (a writable memory) 202 functions as a main memory or a work area of the CPU 201. The CPU 201 implements various kinds of functions and operations by loading a computer program 2031 and basic data, which are for use in processing, from the ROM 203 into the RAM 202 and executing the computer program 2031 to perform processing. The ROM 203 stores, for example, the computer program 2031 and the basic data to be used by the CPU 201 to perform processing. The computer program 2031 may be stored in the external memory 204.

The external memory 204 is a mass-storage device and is implemented by, for example, a hard disk device or an IC memory. The external memory 204 stores, for example, various kinds of data and various kinds of information to be used when the CPU 201 performs processing using the computer program 2031. The external memory 204 also stores, for example, various kinds of data and various kinds of information acquired by the CPU 201 performing processing using the computer program 2031.

The communication I/F (interface) unit 205 is in charge of communication with external apparatuses. The bus is used to communicably connect the CPU 201 to the RAM 202, the ROM 203, the external memory 204, and the communication I/F unit 205.

The control apparatus 110 according to the present exemplary embodiment is provided as a dedicated built-in device, but may be implemented by a general-purpose information processing apparatus such as a personal computer (PC) or a tablet terminal.

FIG. 2B is a functional block diagram illustrating a software configuration of the control apparatus 110 according to the present exemplary embodiment. The control apparatus 110 includes a control unit 211, a communication unit 212, an image acquisition unit 213, a storage unit 214, a receptor field setting unit 215, a threshold value setting unit 216, and a detector rotation setting unit 217. Each of the functions is implemented by the CPU 201 loading the computer program 2031 stored in the ROM 203 into the RAM 202 and executing the computer program 2031.

The control unit 211 determines the presence or absence of various kinds of setting information set in the radiation imaging system 100, and generates and edits the setting information. Alternatively, the control unit 211 functions as an acquisition unit configured to acquire information about the orientation of the radiation detector 115. Alternatively, the control unit 211 functions as a display control unit configured to display information on the display unit 112.

The communication unit 212 communicates with the radiation generation unit 114 and the radiation detector 115 to acquire various kinds of information.

The image acquisition unit 213 acquires a radiation image from the radiation detector 115.

The storage unit 214 stores, for example, various kinds of setting information about the radiation imaging system 100 and various kinds of information acquired by the communication unit 212.

The receptor field setting unit 215 selects a receptor field to be used to measure a radiation dose in the AEC imaging, from among the receptor fields 301 built in the radiation detector 115.

The threshold value setting unit 216 sets a threshold value for the radiation dose to be measured in the receptor fields 301, in order to control the stop of the irradiation with the radiation.

The detector rotation setting unit 217 sets a direction in which the radiation detector 115 to be used in the AEC imaging is rotated. In other words, the detector rotation setting unit 217 is an example of a rotation information setting unit configured to set rotation information about the radiation detector 115.

The above-described functional blocks are merely an example, and the control apparatus 110 may be configured not to include a part of the above-described functional blocks or may be configured to include an additional functional block.

FIG. 4 illustrates an example of a receptor field display form setting screen 401 where the receptor field setting unit 215 and the detector rotation setting unit 217 are displayed on the display unit 112 according to the present exemplary embodiment.

The receptor field display form setting screen 401 includes, for each radiation detector 115 having the built-in AEC function, a receptor field display form setting area 402, receptor field display form options 403, a detector rotation setting area 404, a setting completion instruction area 405, and a setting cancellation instruction area 406.

The receptor field display form setting area 402 is used to set a receptor field display form to be displayed on an imaging screen in the imaging using the radiation detector 115 having the built-in AEC function, and the receptor field display form can be selected from a displayed list of the plurality of receptor field display form options 403. In the receptor field display form setting area 402, the receptor field setting unit 215 can select a receptor field to be used to measure the radiation dose from among the receptor fields 301 built in the radiation detector 115. The selection of the receptor field to be used may be performed on a different setting screen.

Each of the receptor field display form options 403 is an object related to the arrangement of the receptor fields 301 and a mark enabling the identification of the orientation of the radiation detector 115. For example, each of the receptor field display form options 403 is an icon imitating the radiation detector 115 including the plurality of receptor fields 301 for the automatic exposure control and the mark 302 enabling the identification of the orientation of the radiation detector 115.

In the preset exemplary embodiment, the receptor field display form options 403 are merely an example, and may be presented as options not including a display form indicated by the example or may be presented as options including an additional display form. An icon including the same mark as the mark 302 included in the radiation detector 115 to be used in the imaging may be selected, or an icon including a mark different from the mark 302 included in the radiation detector 115 to be used in the imaging may be selected. Alternatively, the icon including the same mark as the mark 302 included in the radiation detector 115 to be used in the imaging may be set as a predetermined icon.

Figure 14:
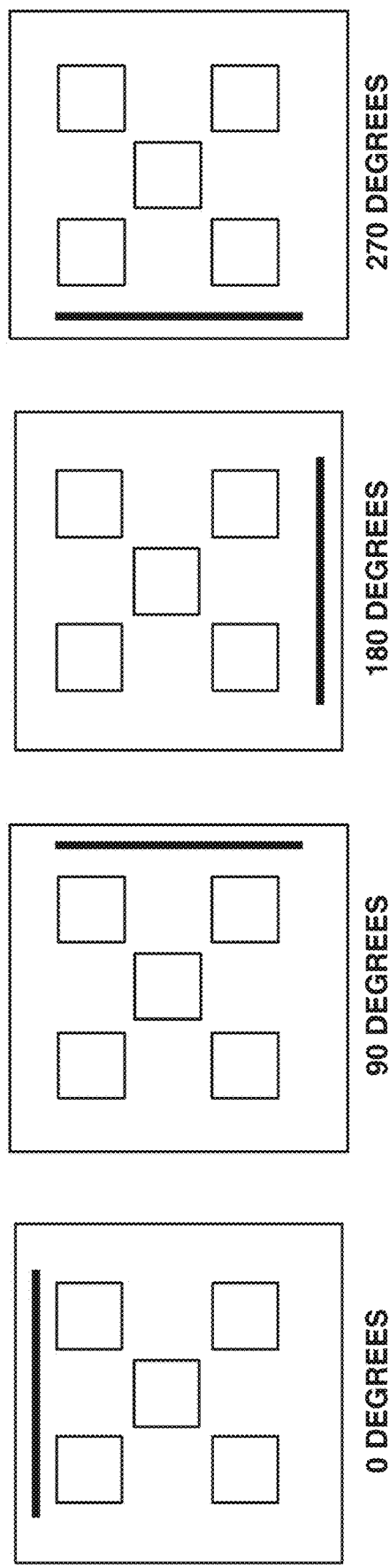
FIG. 14 is a diagram illustrating another example of how the radiation detector display form and the rotation information about the radiation detector are set.

The detector rotation setting area 404 is used to set a rotation direction (a rotation angle) in a direction in a plane containing a radiation detection sensor of the radiation detector 115, which is displayed on the imaging screen in the imaging using the radiation detector 115 having the built-in AEC function. The rotation direction can be selected from a list of pieces of rotation information (e.g., 0 degrees, 90 degrees, 180 degrees, and 270 degrees), such as a combo box. For example, in a case where the lower left icon is used among the four icons displayed in the receptor field display form setting area 402, the respective display forms in which the pieces of rotation information are reflected are indicated as illustrated in FIG. 14. The above-described rotation information is merely an example, and the rate of change and the number of steps can be changed as appropriate.

At this time, the rotation of the radiation detector 115 is to be set based on the rotation of the radiation detector 115 to be performed in actual operation, and a default value thereof is set to no rotation (e.g., 0 degrees). How to select the default value can be changed as appropriate without being limited to the above-described example. For example, a frequently used rotation state (orientation) may be set as the default value, or icons in which rotation states such as those illustrated in FIG. 14 are reflected may be displayed in list form and the operator may select the default value from the displayed list. While the setting of the rotation information in the in-plane direction has been described above, the set information may be information about a posture such as upright or sideways. In other words, the set information is not particularly limited as long as the information indicates the orientation of the radiation detector 115.

The setting completion instruction area 405 is a button for giving an instruction to confirm the setting content of the receptor field display form, and pressing the button causes the setting content to be stored into the storage unit 214.

The setting cancellation instruction area 406 is a button for giving an instruction to cancel the setting content of the receptor field display form.

Figure 5A:
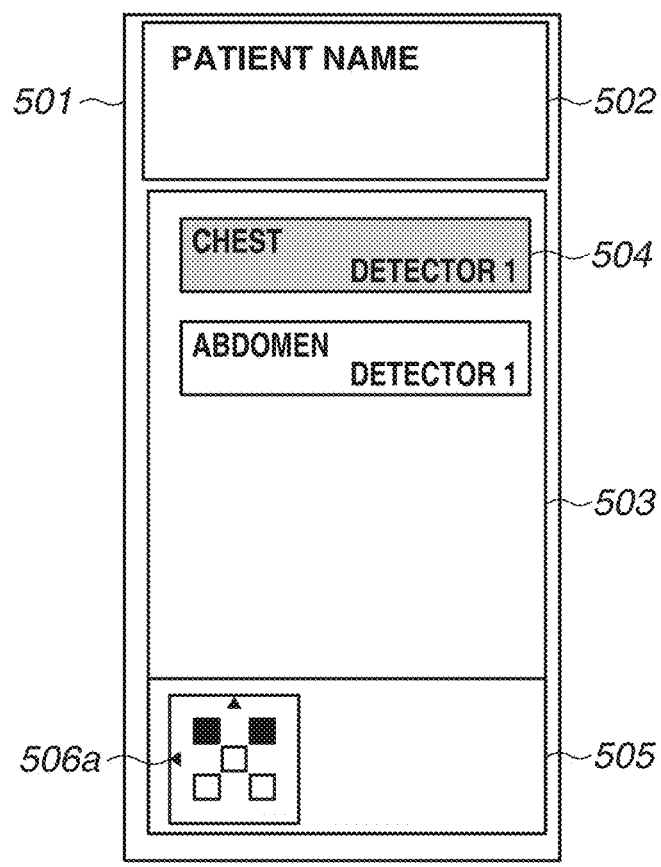
FIGS. 5A and 5B are diagrams each illustrating an example of an examination information display area.
Figure 5B:
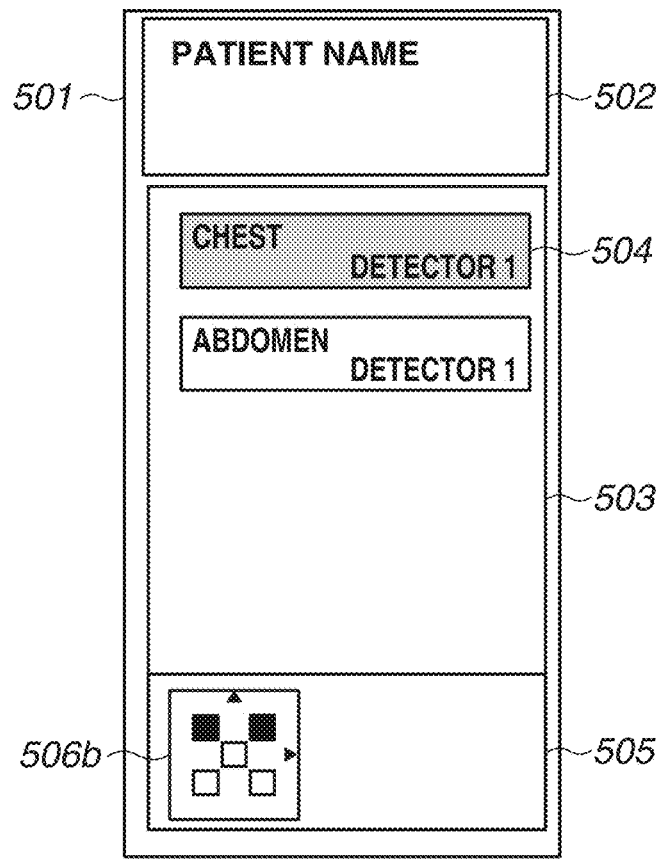

FIGS. 5A and 5B each illustrate an example of an examination information display area 501 displayed on the display unit 112 according to the present exemplary embodiment.

The examination information display area 501 illustrated in FIG. 5A includes a patient information display area 502, an imaging method display area 503, an imaging method 504, an AEC information display area 505, and a receptor field display form 506a.

The patient information display area 502 displays, for example, a name, a gender, and a date of birth of the patient 1000 to be examined.

The imaging method display area 503 displays one or a plurality of the imaging methods 504.

Each imaging method 504 is a button for notifying the radiation detector 115 of imaging method conditions such as an imaging part, an imaging orientation, a type of the radiation detector 115, and AEC setting information, and displays information such as the imaging part, the imaging orientation, and the type of the radiation detector 115.

A display color of the imaging method 504 selected in the imaging can be changed to be distinguished from another imaging method 504.

The AEC information display area 505 displays information about the AEC function built in the radiation detector 115.

The receptor field display form 506a indicates a state where one or a plurality of receptor fields is selected from among the receptor fields 301 of the AEC function built in the radiation detector 115 to be used in each imaging method 504. For example, similarly to the receptor field display form options 403, the receptor field display form 506a is displayed as an icon imitating the radiation detector 115 including the plurality of receptor fields 301 for the automatic exposure control and the mark 302 enabling the identification of the orientation of the radiation detector 115.

FIG. 5B illustrates an example of the examination information display area 501 in a case where the setting value of the rotation information about the radiation detector 115 is changed from the default value.

In the example of FIG. 5B, the setting value of the rotation information about the radiation detector 115 is set to 90 degrees, and the display of the receptor field display form 506a is updated to a receptor field display form 506b indicating that the setting value of the rotation information is 90 degrees.

In this manner, by updating the display of the receptor field display form 506a, which includes a mark such as the mark 302 enabling the identification of the rotation state, based on preset rotation information about the radiation detector 115, it is possible for the operator to easily identify the position(s) of the selected receptor field(s).

Figure 6:
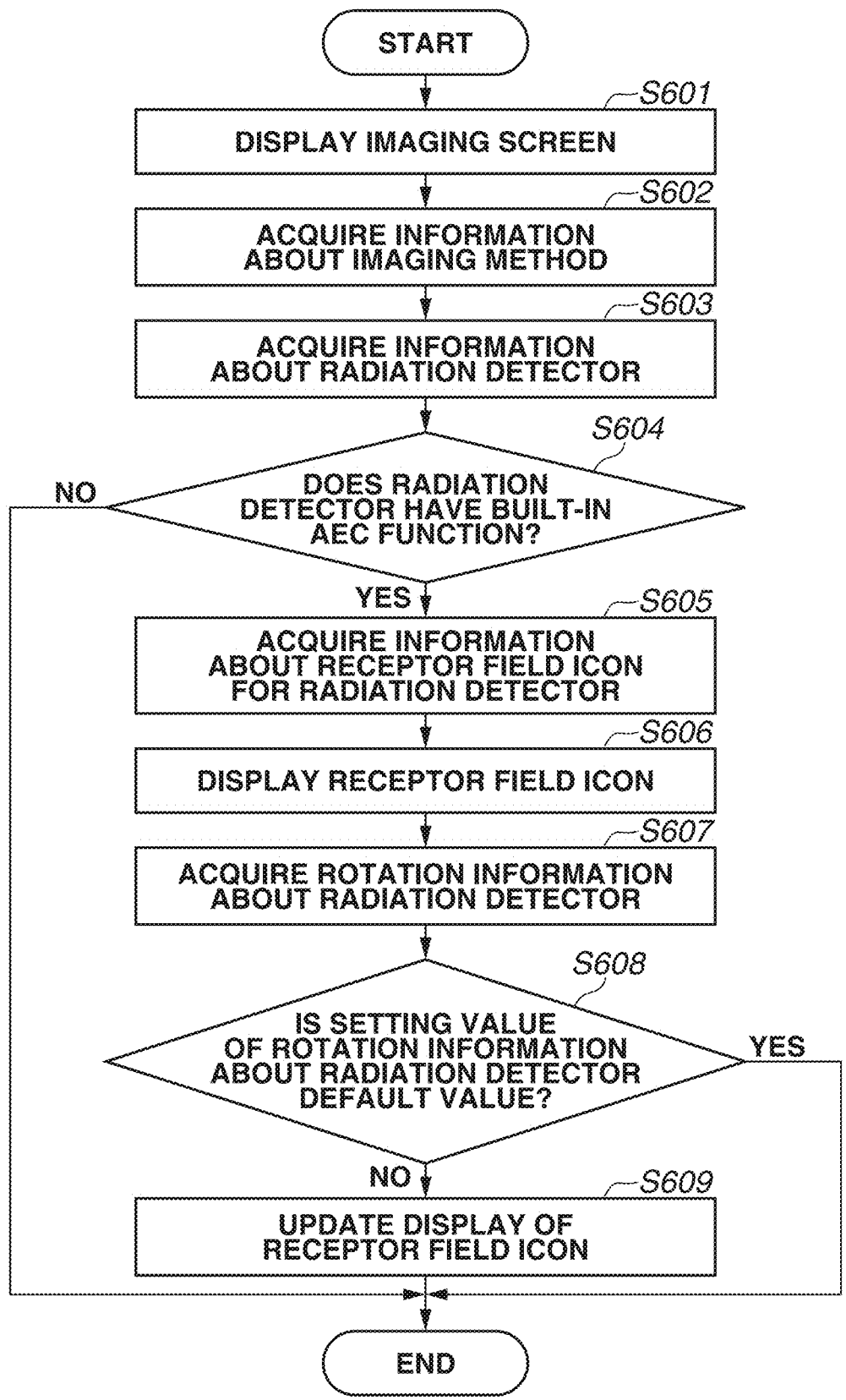
FIG. 6 is a flowchart illustrating processing for enabling an operator to easily identify a position of a selected receptor field.

FIG. 6 is a flowchart illustrating an example of a procedure of processing for enabling the operator to easily identify the position(s) of the selected receptor field(s) when performing the imaging using the radiation detector 115 having the built-in AEC function in the radiation imaging system 100 according to the present exemplary embodiment.
[S601: Transition to Imaging Screen]
In step S601, the control unit 211 displays the imaging screen on the display unit 112.
[S602: Acquisition of Imaging Method Information]
In step S602, the control unit 211 acquires imaging method information from the storage unit 214.
[S603: Acquisition of Radiation Detector Information]
In step S603, the control unit 211 acquires information about the radiation detector 115 to be used in the imaging, from the storage unit 214. At this time, if the control apparatus 110 is not connected to the radiation detector 115, the control unit 211 may determine that the control apparatus 110 is in a state of being not connected to the radiation detector 115, based on the fact that the information about the radiation detector 115 is unable to be acquired. Furthermore, assuming a case where the control apparatus 110 changes from the state of being not connected to the radiation detector 115 to the state of being connected to the radiation detector 115, the processing in step S603 may be repeated at predetermined intervals until the radiation detector 115 is connected.
[S604: Determination of Whether Radiation Detector has Built-In AEC Function]
In step S604, the control unit 211 determines whether the radiation detector 115 has the built-in AEC function, based on the information acquired in step S603.

If the radiation detector 115 has the built-in AEC function (YES in step S604), the processing proceeds to step S605. If the radiation detector 115 does not have the built-in AEC function (NO in step S604), the processing ends. At this time, if the control apparatus 110 is in the state of being not connected to the radiation detector 115, the control unit 211 may determine that the radiation detector 115 does not have the built-in AEC function.
[S605: Acquisition of Information about Receptor Field Icon for Radiation Detector)
In step S605, the control unit 211 acquires, from the storage unit 214, information about the receptor field display form 506a that includes a receptor field to be used for the automatic exposure control, which is preset by the receptor field setting unit 215, and the mark 302 enabling the identification of the orientation of the radiation detector 115.
[S606: Display of Receptor Field Icon]
In step S606, the control unit 211 displays the AEC information display area 505 and the receptor field display form 506a based on the information acquired in step S605, on the examination information display area 501.
[S607: Acquisition of Rotation Information about Radiation Detector]
In step S607, the control unit 211 acquires, from the storage unit 214, the rotation information about the radiation detector 115 that is set by the detector rotation setting unit 217. In other words, the control unit 211 acquires information about the orientation of the radiation detector 115.
[S608: Determination of Whether Setting Value of Rotation Information about Radiation Detector is Default Value]
In step S608, the control unit 211 determines whether the setting value of the rotation information about the radiation detector 115 acquired in step S607 is the default value. If the setting value of the rotation information is the default value (YES in step S608), the processing ends. If the setting value of the rotation information is not the default value (NO in step S608), the processing proceeds to step S609.

[S609: Update of Display of Receptor Field Icon]

In step S609, the control unit 211 updates the receptor field display form 506a displayed in the AEC information display area 505 to the receptor field display form 506b, based on the setting value of the rotation information about the radiation detector 115 acquired in step S607. More specifically, for example, the control unit 211 updates the display so as to rotate the icon by the rotation angle in a case where the rotation angle as the setting value is a value other than 0 degrees (e.g., 90 degrees).

Then, the processing in the flowchart of FIG. 6 ends.

As described above, in the present exemplary embodiment, the display of the receptor field display form 506a is updated based on the rotation information about the radiation detector 115 preset by the detector rotation setting unit 217, whereby the actual rotation state of the radiation detector 115 and the state of the selected receptor field(s) can match each other.

As a result, the operator can easily identify the position(s) of the selected receptor field(s). Moreover, in the imaging using the radiation imaging apparatus having the built-in AEC function, the operator can select a plurality of receptor fields to be used for the automatic exposure control and easily identify the positions of the selected receptor fields.

In the present exemplary embodiment, the configuration in which, after the receptor field display form 506a is displayed in step S606, the rotation information is acquired in step S607, and the receptor field display form 506a is updated in step S609. Alternatively, in step S606, the control unit 211 may also acquire the rotation information from the storage unit 214 and display the receptor field display form 506b without displaying the receptor field display form 506a, based on the acquired rotation information.

According to the above-described configuration, the operator can easily identify the position(s) of the selected receptor field(s). Furthermore, in the imaging using the radiation imaging apparatus having the built-in AEC function, the operator can select a plurality of receptor fields to be used for the automatic exposure control and easily identify the positions of the selected receptor fields.

In the first exemplary embodiment, the example of updating the display of the receptor field display form 506a based on the preset rotation information about the radiation detector 115 has been described.

In a second exemplary embodiment, an example of presenting a plurality of candidates each having one or a plurality of preselected receptor fields at the time of receptor field selection will be described.

Configurations of the radiation imaging system 100 and the control apparatus 110 according to the present exemplary embodiment are similar to those according to the first exemplary embodiment, and thus the detailed descriptions thereof will be omitted.

Conventionally, to change a receptor field selection state in the AEC imaging, the operator is to set each of the receptor fields 301 to be enabled or disabled individually. Meanwhile, in the imaging using the AEC function built in the radiation detector 115, the number of receptor fields 301 arranged in the radiation detector 115 may differ depending on the type of radiation detector 115.

In this case, some specific type of radiation detector 115 including a large number of receptor fields 301 built therein may lead to a reduction in imaging flow efficiency because the operator is to set each of the receptor fields 301 to be enabled or disabled individually.

To address the issue, in the present exemplary embodiment, a plurality of candidates each having one or a plurality of preselected receptor fields is presented at the time of receptor field selection. This configuration makes it possible to save time to set each of the receptor fields 301 to be enabled or disabled individually and thus improve the imaging flow efficiency even in the AEC imaging using the radiation detector 115 including a large number of receptor fields 301 built therein.

Figure 7:
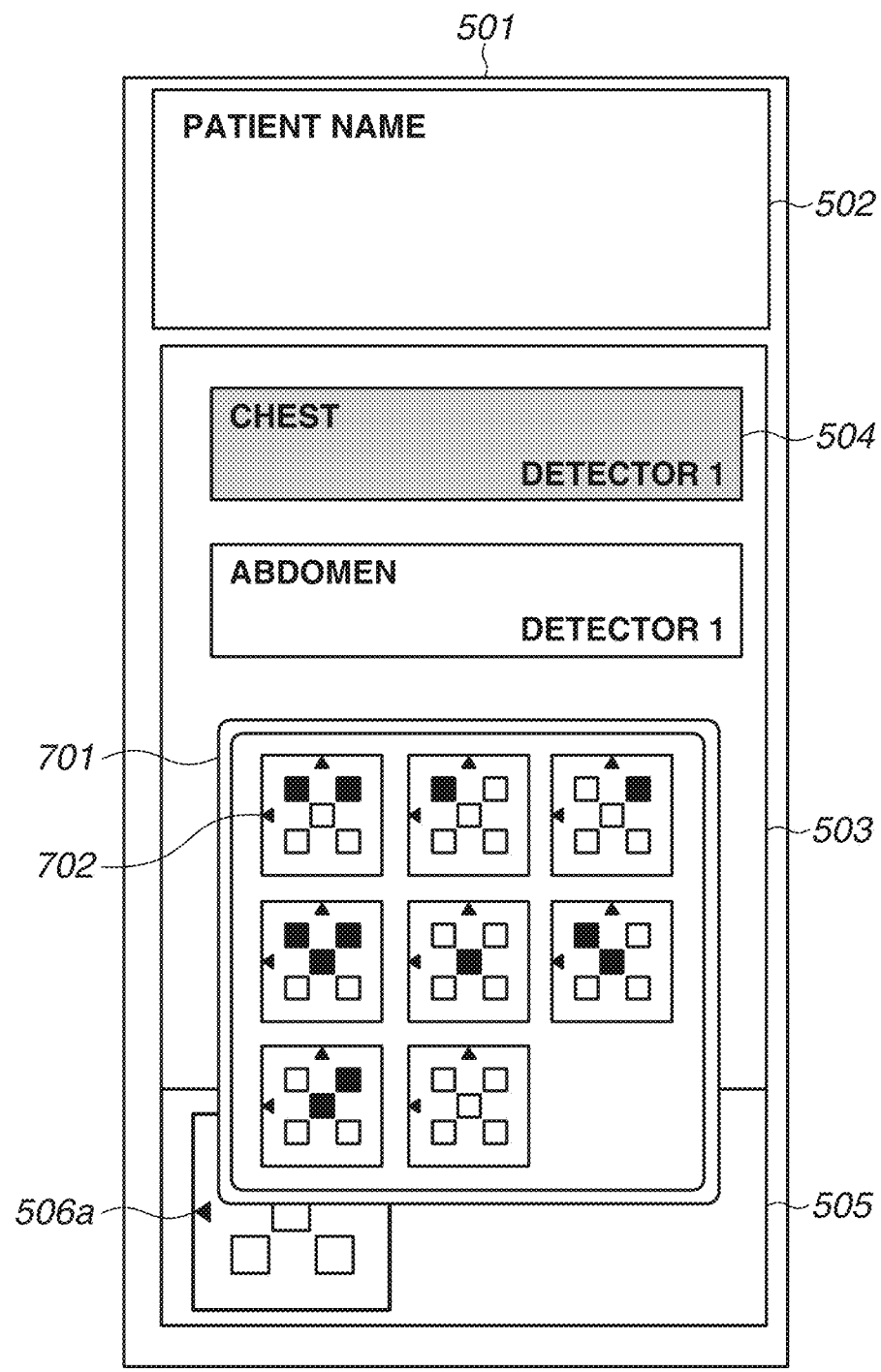
FIG. 7 is a diagram illustrating an example of a receptor field candidate option dialog.

FIG. 7 illustrates an example of the examination information display area 501 displayed on the display unit 112 according to the present exemplary embodiment. Elements similar to those illustrated in FIGS. 5A and 5B will be denoted by the same reference numerals, and thus the detailed descriptions thereof will be omitted.

A receptor field candidate dialog 701 (a receptor field setting screen) illustrated in FIG. 7 is displayed in response to pressing of the receptor field display form 506a or 506b.

Receptor field candidate options 702 are displayed as a plurality of buttons in the receptor field candidate dialog 701. When one of the receptor field candidate options 702 is pressed, the state of the selected receptor field(s) is updated.

In the receptor field candidate dialog 701, the receptor field candidate options 702 are displayed with different receptor field selection states depending on the radiation detector 115 to be used in the imaging. The receptor field candidate dialog 701 may display some of combinations of the selection states. Alternatively, the receptor field candidate dialog 701 may display all combinations of the selection states. In a case where a display area of the receptor field candidate dialog 701 is not sufficient to display all the combinations of the selection states, the receptor field candidate dialog 701 may be configured to display receptor field candidates more likely to be selected, with higher priority, and display low-priority receptor field candidates by being scrolled. The above-described configuration is merely an example, and the receptor field candidate dialog 701 may be configured to be enlarged or reduced depending on the number of combinations.

Figure 8:
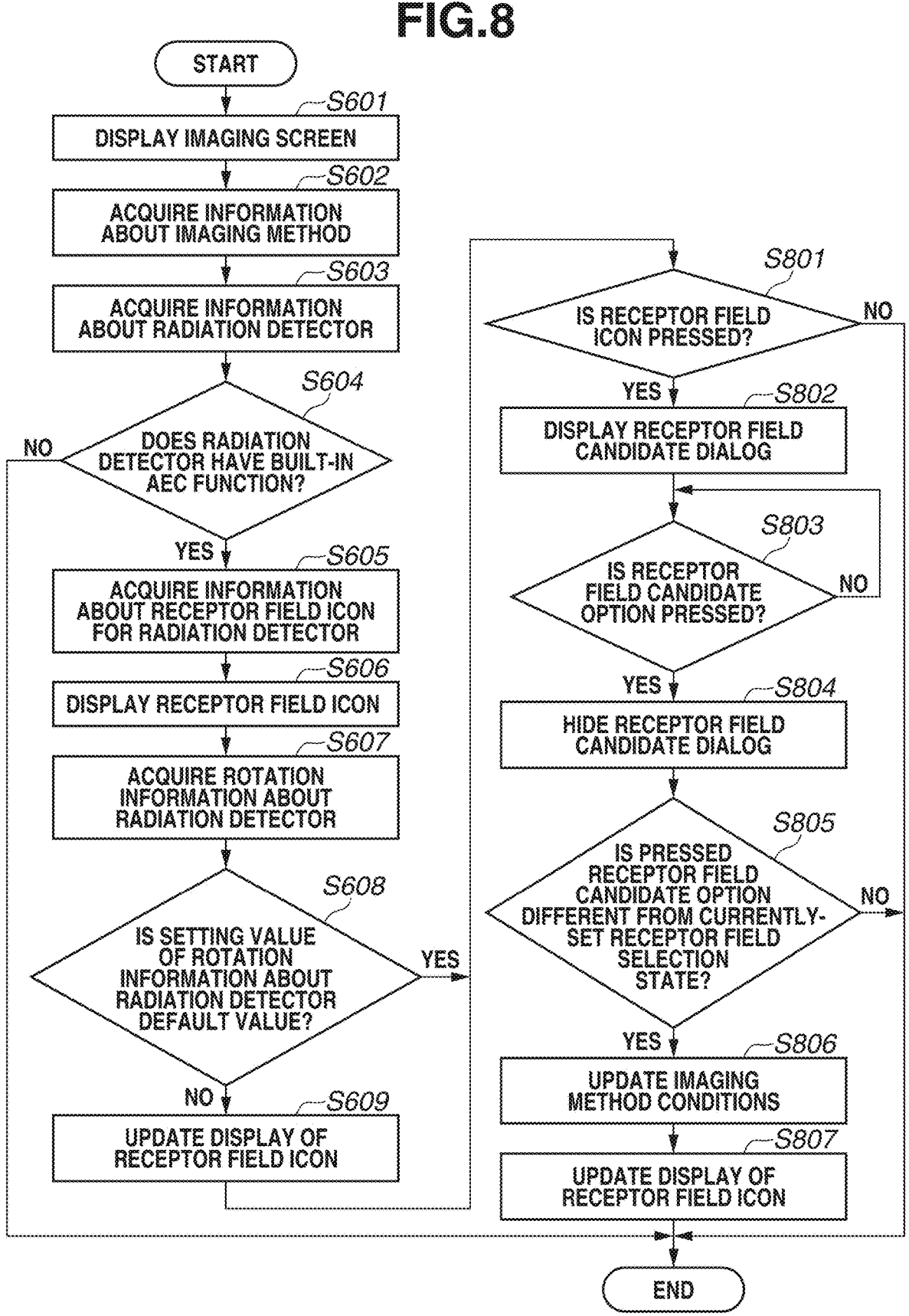
FIG. 8 is a flowchart illustrating processing for displaying the receptor field candidate option dialog.

FIG. 8 is a flowchart illustrating a procedure of processing according to the present exemplary embodiment. Processing similar to the processing in FIG. 6 is denoted by the same step numbers, and thus the detailed descriptions thereof will be omitted.

[S801: Determination of Whether Receptor Field Icon is Pressed]

In step S801, the control unit 211 determines whether the receptor field display form 506a is pressed, based on an operation performed via the operation unit 113.

If the receptor field display form 506a is pressed (YES in step S801), the processing proceeds to step S802. If the receptor field display form 506a is not pressed (NO in step S801), the processing ends.

[S802: Display of Receptor Field Candidate Dialog]

In step S802, the control unit 211 displays the receptor field candidate dialog 701 on the display unit 112.

[S803: Determination of Whether Receptor Field Candidate Option is Pressed]

In step S803, the control unit 211 determines whether one of the receptor field candidate options 702 displayed on the receptor field candidate dialog 701 is pressed, based on an operation performed via the operation unit 113.

If one of the receptor field candidate options 702 is pressed (YES in step S803), the processing proceeds to step S804. If none of the receptor field candidate options 702 are pressed (NO in step S803), the control unit 211 waits until one of the receptor field candidate options 702 is pressed.

[S804: Hiding of Receptor Field Candidate Dialog]

In step S804, the control unit 211 hides the receptor field candidate dialog 701 displayed on the display unit 112.

[S805: Determination of Whether Pressed Receptor Field Candidate Option is Different from Currently-Set Receptor Field Selection State]

In step S805, the control unit 211 determines whether the receptor field candidate option 702 pressed on the receptor field candidate dialog 701 is different from the currently-set receptor field selection state.

If the pressed receptor field candidate option 702 is different from the currently-set receptor field selection state (YES in step S805), the processing proceeds to step S806. If the pressed receptor field candidate option 702 is the same as the currently-set receptor field selection state (NO in step S805), the processing ends.

[S806: Update of Imaging Method Conditions]

In step S806, the control unit 211 updates the AEC setting information in the imaging method conditions, based on the selection state of the receptor field candidate option 702 pressed in step S803.

[S807: Update of Display of Receptor Field Icon]

In step S807, the control unit 211 updates the display of the receptor field display form 506a in the AEC information display area 505, based on the selection state of the receptor field candidate option 702 pressed in step S803.

Then, the processing in the flowchart of FIG. 8 ends.

As described above, a plurality of candidates each having one or a plurality of preselected receptor fields is presented in the present exemplary embodiment. This configuration makes it possible to save time to set each of the receptor fields 301 to be enabled or disabled individually and thus improve the imaging flow efficiency even in the AEC imaging using the radiation detector 115 including a large number of receptor fields 301 built therein.

In the second exemplary embodiment, the example of presenting a plurality of candidates each having one or a plurality of preselected receptor fields at the time of receptor field selection has been described.

In a third exemplary embodiment, an example of enabling setting of the candidates based on the imaging part at the time of receptor field selection will be described.

Configurations of the radiation imaging system 100 and the control apparatus 110 according to the present exemplary embodiment are similar to those according to the first exemplary embodiment, and thus the detailed descriptions thereof will be omitted.

Generally, one or a plurality of receptor fields to be selected depends on the imaging part. For example, if the imaging part is a chest, a receptor field corresponding to the position of a lung field is selected. Thus, in one embodiment, receptor field selection candidates based on the imaging part are to be displayed.

Figure 9A:
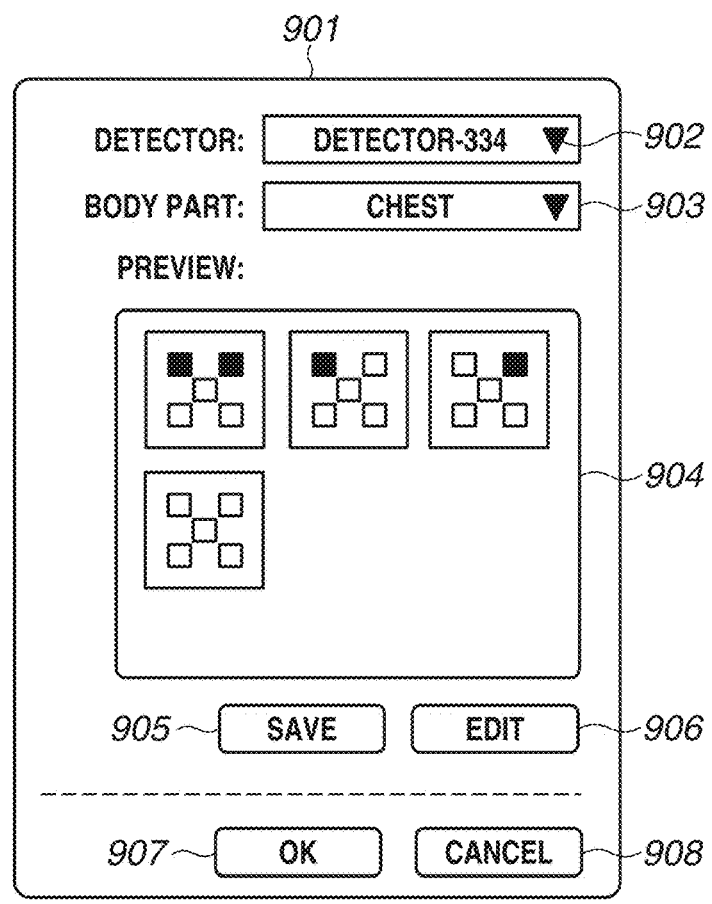
FIGS. 9A and 9B are diagrams illustrating an example of how receptor field candidate options are edited based on a type of the radiation detector and an imaging part.
Figure 9B:
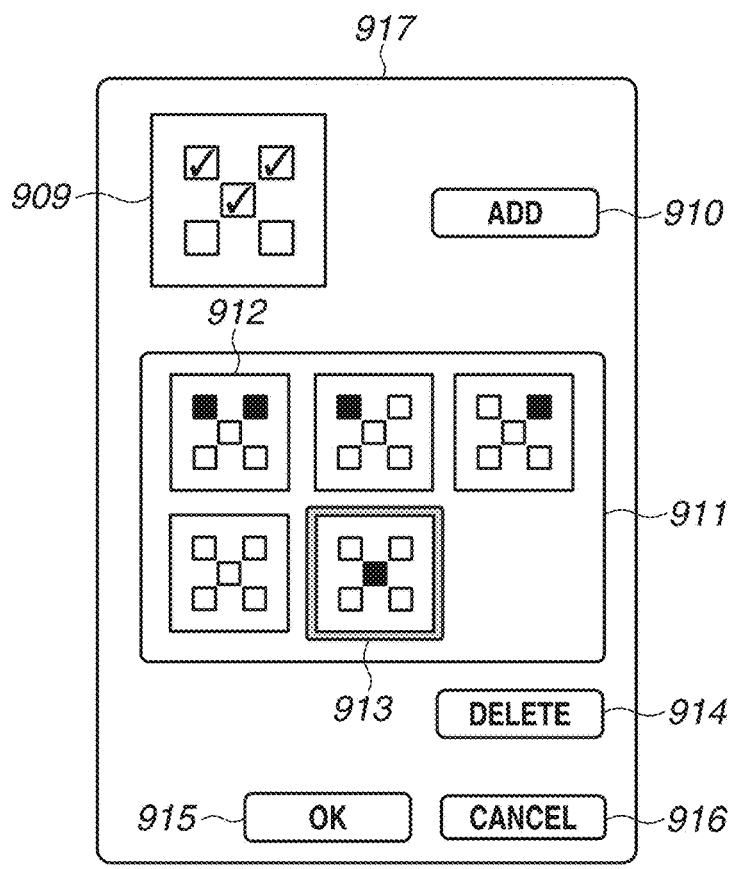

FIGS. 9A and 9B illustrate an example in which the receptor field setting unit 215 according to the present exemplary embodiment sets the receptor field candidate options 702 to be displayed on the receptor field candidate dialog 701 displayed on the display unit 112.

A receptor field selection candidate editing screen 901 illustrated in FIG. 9A includes a radiation detector type selection area 902, an imaging part selection area 903, a receptor field selection candidate preview area 904, a receptor field selection candidate storage area 905, a receptor field option editing area 906, an edited setting completion instruction area 907, and an edited setting cancellation instruction area 908.

The radiation detector type selection area 902 is used to select one of the radiation detectors 115 registered in the radiation imaging system 100, and the radiation detector 115 can be selected from a list such as a combo box. At this time, the radiation detector type selection area 902 may display the radiation detector(s) 115 having the built-in AEC function among the radiation detectors 115 registered in the radiation imaging system 100.

The imaging part selection area 903 is used to select the imaging part, and the imaging part can be selected from a list such as a combo box.

The receptor field selection candidate preview area 904 is used to preview a display example of the list of the receptor field candidate options 702 to be displayed in the receptor field candidate dialog 701. The display of the receptor field candidate options 702 is updated for each item selected in the radiation detector type selection area 902 or the imaging part selection area 903. At this time, a desired list of the receptor field candidate options 702 may be displayed as a default value.

The receptor field selection candidate storage area 905 is a button for giving an instruction to save the contents that are currently being set during the editing of the receptor field selection candidates.

The receptor field option editing area 906 is a button for giving an instruction to display a receptor field option editing dialog 917.

The edited setting completion instruction area 907 is a button for giving an instruction to confirm the setting contents of the editing of the receptor field selection candidates, and pressing the button causes the setting contents to be stored into the storage unit 214.

The edited setting cancellation instruction area 908 is a button for giving an instruction to cancel the setting contents of the editing of the receptor field selection candidates.

The receptor field option editing dialog 917 illustrated in FIG. 9B includes a receptor field enable selection area 909, a receptor field option addition area 910, a receptor field candidate list area 911, receptor field option display forms 912, an option deletion candidate display form 913, a receptor field option deletion area 914, an option editing completion instruction area 915, and an option editing cancellation instruction area 916.

The receptor field enable selection area 909 is used to select a receptor field to be enabled, from, for example, check boxes imitating the arrangement of the receptor fields 301 built in the actual radiation detector 115, based on the selection in the radiation detector type selection area 902.

The receptor field option addition area 910 is a button for giving an instruction to add a receptor field option candidate, and pressing the button causes the selection state in the receptor field enable selection area 909 to be added as a receptor field option candidate.

The receptor field candidate list area 911 displays the list of receptor field option candidates.

Each of the receptor field option display forms 912 is the display form of a receptor field option candidate, and is displayed in the receptor field candidate list area 911.

The option deletion candidate display form 913 indicates a display form to be deleted from the list of receptor field option candidates. A desired one selected from the receptor field option display forms 912 displayed in the receptor field candidate list area 911 is displayed as the option deletion candidate display form 913 indicating the display form to be deleted.

The receptor field option deletion area 914 is a button for giving an instruction to delete a receptor field option candidate, and pressing the button causes the option deletion candidate display form 913 to be deleted from the receptor field candidate list area 911. If the option deletion candidate display form 913 is not present in the receptor field candidate list area 911, the receptor field option deletion area 914 is disabled.

The option editing completion instruction area 915 is a button for giving an instruction to confirm the setting contents in the receptor field option editing dialog 917, and pressing the button causes the receptor field option editing dialog 917 to be closed and the setting contents to be stored into the storage unit 214.

The option editing cancellation instruction area 916 is a button for giving an instruction to cancel the setting contents in the receptor field option editing dialog 917, and pressing the button causes the receptor field option editing dialog 917 to be closed.

Figure 10:
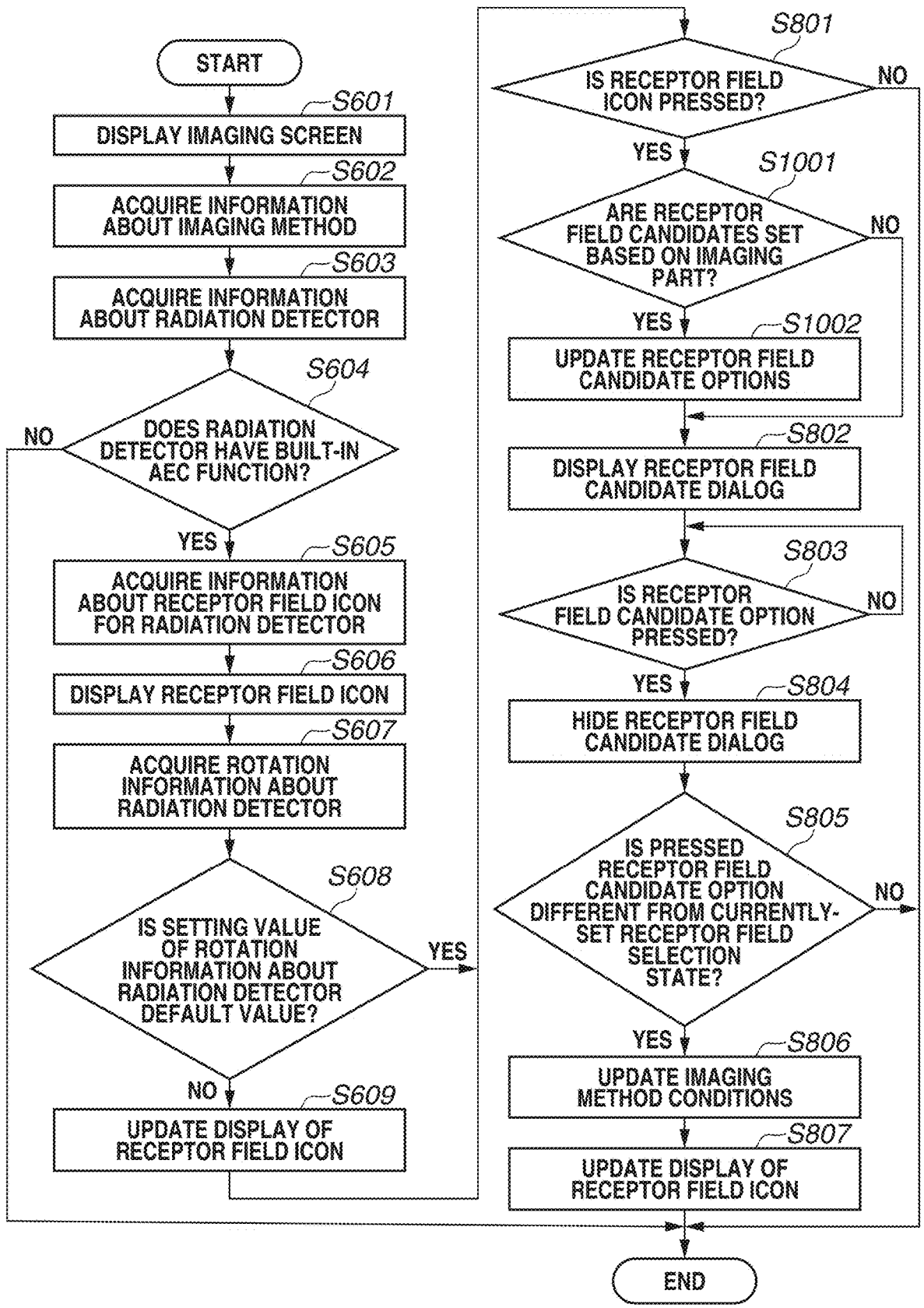
FIG. 10 is a flowchart illustrating processing for displaying the receptor field candidate options based on the type of the radiation detector and the imaging part.

FIG. 10 is a flowchart illustrating a procedure of processing according to the present exemplary embodiment. Processing similar to the processing in FIG. 8 is denoted by the same step numbers, and thus the detailed descriptions thereof will be omitted.

[S1001: Determination of Whether Receptor Field Candidates are Set Based on Imaging Part]

In step S1001, the control unit 211 determines whether the setting of the receptor field candidates based on the imaging part is stored in the storage unit 214, based on the information about the imaging part in the imaging method conditions (the imaging method information) acquired in step S602.

If the setting of the receptor field candidates based on the imaging part is stored (YES in step S1001), the processing proceeds to step S1002. If the setting of the receptor field candidates based on the imaging part is not stored (NO in step S1002), the processing proceeds to step S802.

[S1002: Update of Receptor Field Candidate Options]

In step S1002, the control unit 211 acquires the setting contents of the editing of the receptor field selection candidates from the storage unit 214, and updates the receptor field candidate options 702 based on the setting contents.

Then, the processing in the flowchart of FIG. 10 ends.

As described above, in the present exemplary embodiment, the receptor field selection candidates preset depending on the radiation detector 115 and the imaging part are presented. This makes it possible to save time to set each of the receptor fields 301 to be enabled or disabled individually, thereby contributing to not only further increasing the imaging flow efficiency but also preventing the selection of a receptor field not corresponding to the position of the imaging part.

In the first exemplary embodiment, the example of updating the display of the receptor field display form 506*a* based on the preset rotation information about the radiation detector 115 has been described.

In a fourth exemplary embodiment, an example of updating the display of the receptor field display form 506*a* by changing the rotation information about the radiation detector 115 during the examination.

Configurations of the radiation imaging system 100 and the control apparatus 110 according to the present exemplary embodiment are similar to those according to the first exemplary embodiment, and thus the detailed descriptions thereof will be omitted.

Generally, depending on the imaging environment or the condition of the patient 1000, the imaging may be performed after the radiation detector 115 is rotated even when the rotation information about the radiation detector is set in advance. Thus, in one embodiment, the rotation information about the radiation detector 115 can be changed during the examination.

Figure 11:
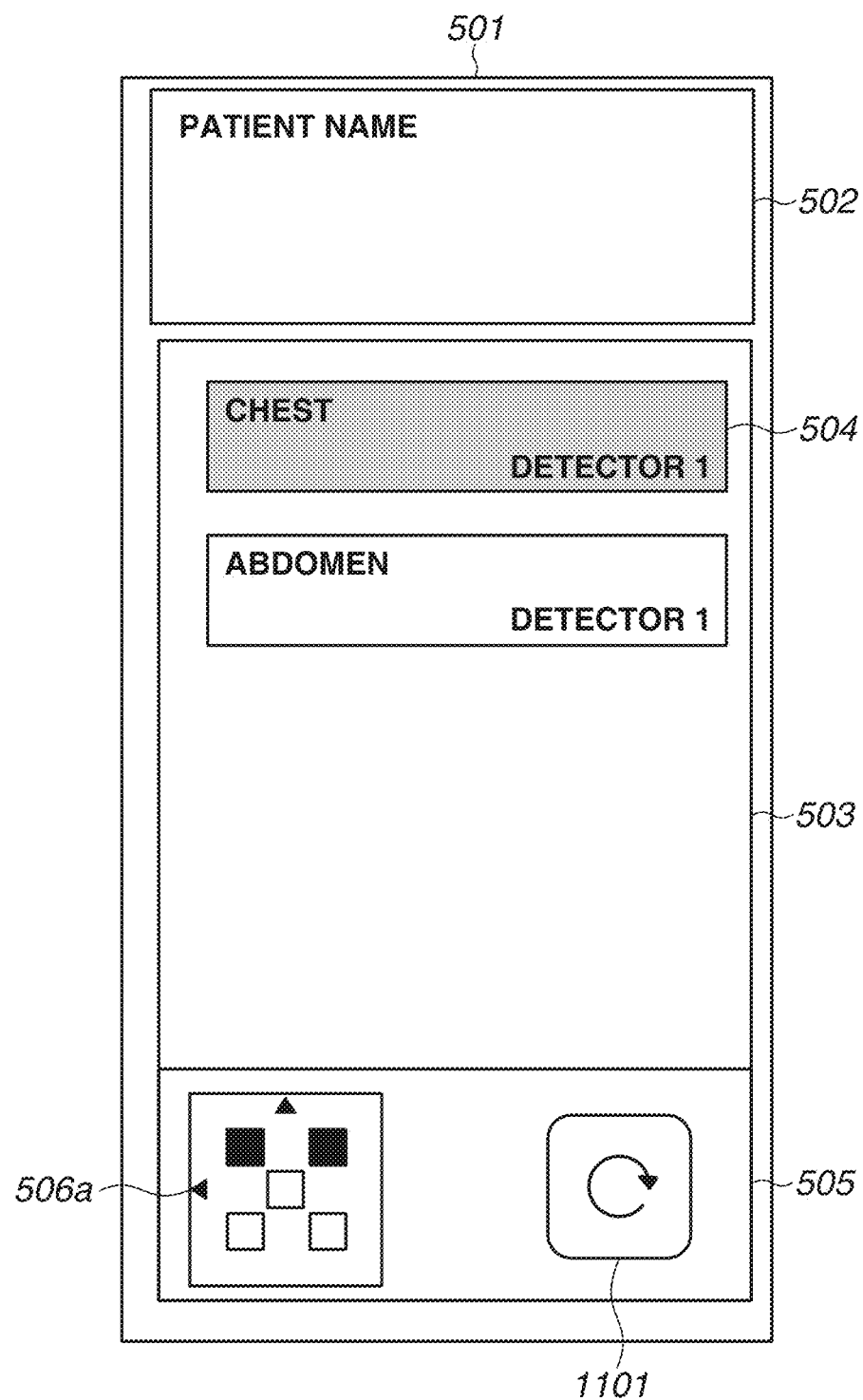
FIG. 11 is a diagram illustrating an example of how the rotation information about the radiation detector is updated during examination.

FIG. 11 illustrates an example of the examination information display area 501 displayed on the display unit 112 according to the present exemplary embodiment.

The AEC information display area 505 illustrated in FIG. 11 includes a rotation information update area 1101. The rotation information update area 1101 is a button for giving an instruction to update the rotation information about the radiation detector 115, and pressing the button causes the setting value of the rotation information to be updated and the display of the receptor field display form 506*a* to be updated. More specifically, the button for receiving the update of the rotation information from the operator is displayed on the display unit 112 together with the icon. For example, each time the button is pressed, the setting value of the rotation information is changed by 90 degrees and the receptor field display form 506*a* can be updated to the receptor field display form 506*b*.

At this time, the display of the receptor field candidate options 702 displayed in the receptor field candidate dialog 701 can also be updated.

Figure 12:
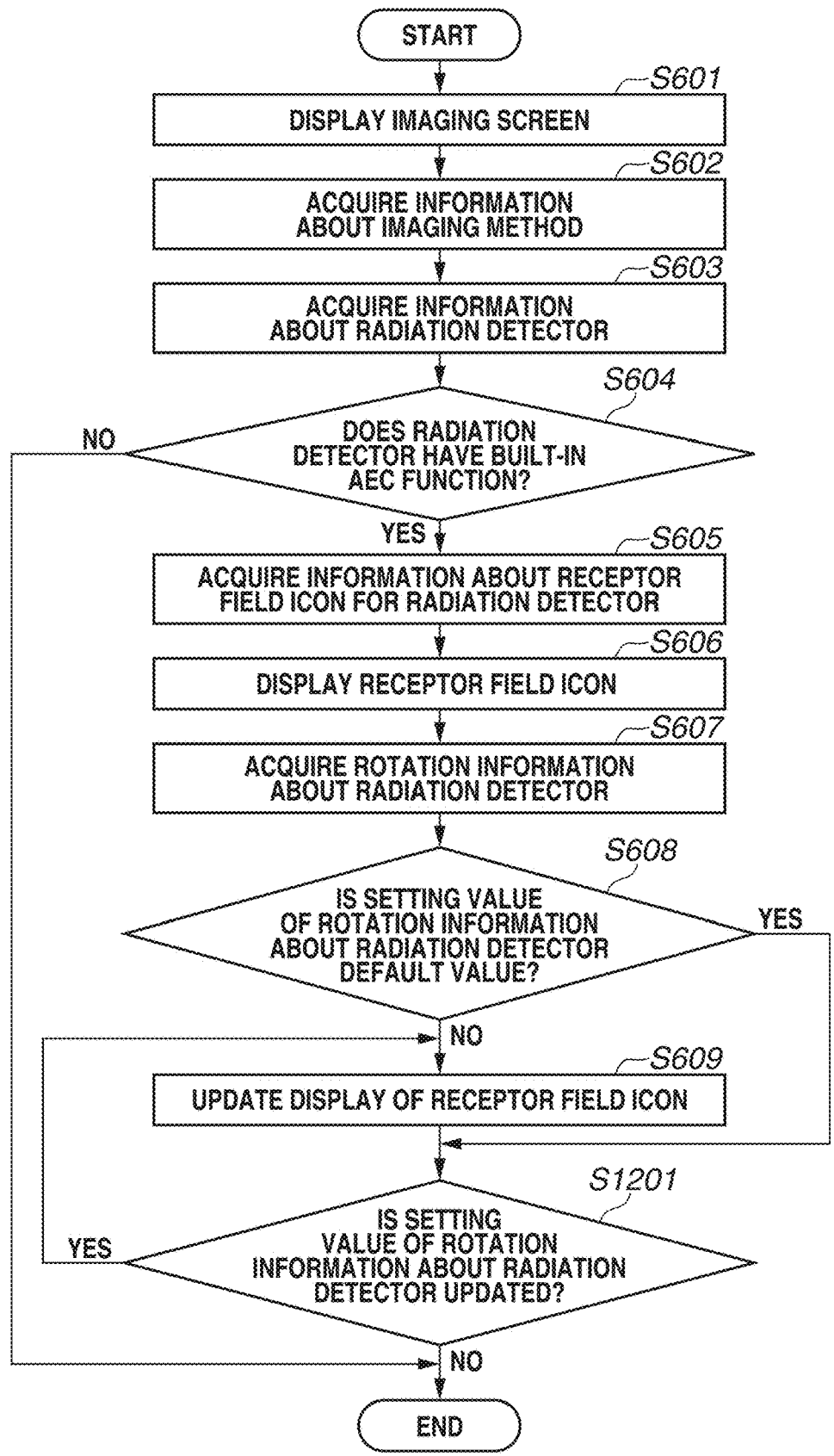
FIG. 12 is a flowchart illustrating processing for updating the rotation information about the radiation detector during the examination.

FIG. 12 is a flowchart illustrating a procedure of processing according to the present exemplary embodiment. Processing similar to the processing in FIG. 6 is denoted by the same step numbers, and thus the detailed descriptions thereof will be omitted.

[S1201: Determination of Whether Setting Value of Rotation Information about Radiation Detector is Updated]

In step S1201, the control unit 211 determines whether the rotation information update area 1101 is pressed, based on an operation performed via the operation unit 113.

If the rotation information update area 1101 is pressed (YES in step S1201), the processing proceeds to step S609. If the rotation information update area 1101 is not pressed (NO in step S1201), the processing ends.

Then, the processing in the flowchart of FIG. 10 ends.

As described above, in the present exemplary embodiment, the rotation information about the radiation detector 115 can be changed during the examination. This makes it possible to match the state of the selected receptor field(s) and the display of the receptor field display form 506*a* with the actual rotation state of the radiation detector 115 even when the radiation detector 115 is rotated due to the imaging environment or the condition of the patient 1000.

As a result, the operator can easily identify the position(s) of the selected receptor field(s).

In the first exemplary embodiment, the example of updating the display of the receptor field display form 506*a* based on the preset rotation information about the radiation detector 115 has been described.

In a fifth exemplary embodiment, an example in which a detection unit (not illustrated) for detecting the orientation of the radiation detector 115 is included in the radiation detector 115, and the display of the receptor field display form 506*a* is updated based on information about the orientation detected by the detection unit.

Configurations of the radiation imaging system 100 and the control apparatus 110 according to the present exemplary embodiment are similar to those according to the first exemplary embodiment, and thus the detailed descriptions thereof will be omitted.

Processing according to the present exemplary embodiment will be described with reference to FIGS. 13A to 13C.

Figure 13A:
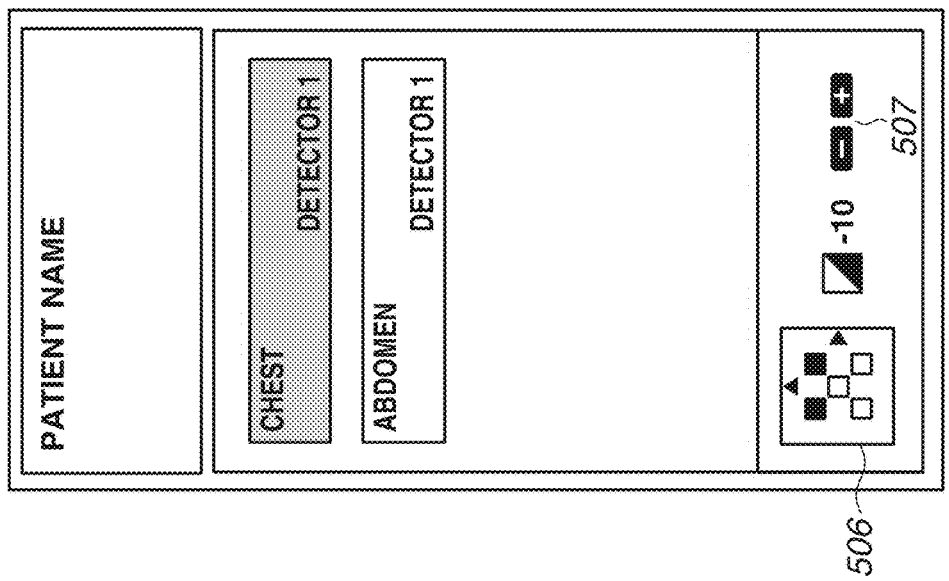
FIGS. 13A to 13C are diagrams each illustrating another example of the examination information display area.
Figure 13B:
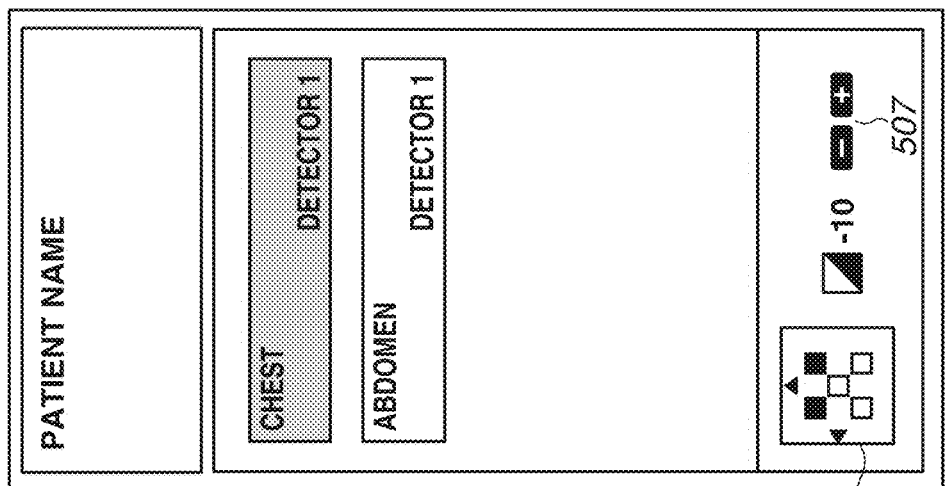
Figure 13C:
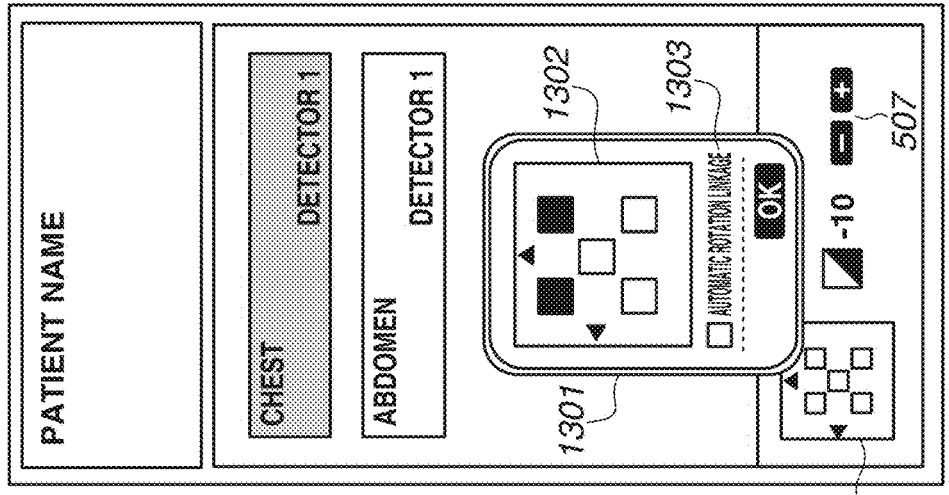

FIGS. 13A to 13C illustrate an example of the examination information display area 501 in a case where the radiation detector 115 including the detection unit for detecting the orientation is used. Elements similar to those illustrated in FIGS. 5A and 5B will be denoted by the same reference numerals, and thus the detailed descriptions thereof will be omitted. The examination information display area 501 illustrated in each of FIGS. 13A to 13C further includes a threshold value adjustment area 507. A threshold value for the stop of the automatic exposure control (AEC) can be set in the threshold value adjustment area 507. In the present exemplary embodiment, the threshold value adjustment area 507 indicates an example in which the threshold value is incremented by pressing a plus button and is decremented by pressing a minus button. The above-described configuration is merely an example, and the threshold value adjustment area 507 is not limited thereto. The rate of change and the number of steps can be changed as appropriate.

A receptor field candidate dialog 1301 illustrated in FIG. 13A is displayed when a receptor field display form 506 is pressed or a cursor is placed on the receptor field display form 506. The receptor field candidate dialog 1301 includes a receptor field option 1302 and a rotation linkage setting portion 1303.

The receptor field option 1302 according to the present exemplary embodiment uses a method in which the operator selects a desired receptor field to be used for the automatic exposure control from among the plurality of receptor fields 301 built in the radiation detector 115. For example, if the operator selects the upper left receptor field and the upper right receptor field from among the selectable five receptor fields 301 as illustrated in FIG. 13A, the display of the selected receptor fields is changed. The receptor field option 1302 may not necessarily use the method in which the operator selects a desired receptor field to be used from among the plurality of receptor fields 301, and may use a method in which a plurality of predetermined combinations of the plurality of receptor fields 301 is displayed as illustrated in FIG. 7 and the operator selects one of the plurality of predetermined combinations. Alternatively, the operator can select which method to use. More specifically, the receptor field option 1302 may enable the operator to select or switch between the setting screen for setting a receptor field to be used from among the plurality of predetermined combinations of the plurality of receptor fields 301, and the setting screen for enabling the operator to manually set a receptor field to be used from among the plurality of receptor fields 301.

The rotation linkage setting portion 1303 is used to set whether to update the receptor field display form 506 based on the information about the orientation detected by the detection unit. In the present exemplary embodiment, the rotation linkage setting portion 1303 is described as a button capable of switching on or off the rotation linkage setting.

Processing performed in a case where the rotation linkage setting portion 1303 is used to set the receptor field display form 506 to be updated based on the information about the orientation detected by the detection unit (in a case where the automatic rotation linkage is set to ON) will be described.

First, on the receptor field option 1302 in FIG. 13A, the operator selects one or a plurality of receptor fields to be used for the automatic exposure control (e.g., the upper left receptor field and the upper right receptor field). The operator also sets the automatic rotation linkage to ON.

After the receptor fields to be used are selected by the operator, the result of the selection is reflected in the receptor field display form 506 as illustrated in FIG. 13B.

If the orientation of the radiation detector 115 is, for example, tilted by 90 degrees in the state of FIG. 13B, the detection unit detects the tilt of the radiation detector 115 and transmits the information about the detected orientation of the radiation detector 115 to the control unit 211. Then, the control unit 211 acquires the information about the orientation of the radiation detector 115 detected by the detection unit, and updates the display of the receptor field display form 506 to a state rotated by 90 degrees as illustrated in FIG. 13C. More specifically, the control unit 211 displays the icon on the display unit 112 based on the information about the orientation of the radiation detector 115 detected by the detection unit.

As the method for detecting the orientation of the radiation detector 115, the radiation detector 115 is configured to include, for example, an acceleration sensor or a gyroscope sensor as the detection unit. The orientation can be calculated based on acceleration that is a value output from the acceleration sensor or an angular velocity that is a value output from the gyroscope sensor. More specifically, for example, the calculation of the orientation using the gyroscope sensor is performed by summing (integrating) the angular velocity in a short time that is measured using the gyroscope sensor. The calculation of the orientation using the acceleration sensor is carried out by once integrating the acceleration measured using the acceleration sensor to calculate a speed at a certain time, and further integrating the speed to calculate a displacement (a position). The method for detecting the orientation of the radiation detector 115 is not limited thereto, and the orientation of the radiation detector 115 may be detected, for example, using an angular velocity sensor or a geomagnetic sensor. Alternatively, the orientation of the radiation detector 115 may be determined from an image captured by an imaging unit such as a camera provided in a radiation imaging apparatus including a radiation generation apparatus and the radiation detector 115. In this case, the image captured by the imaging unit is transmitted to the control unit 211, and the orientation of the radiation detector 115 is determined by a not-illustrated determination unit. Processing for determining the orientation of the radiation detector 115 by the determination unit can be implemented by various known methods.

In a case where the operator desires to change the receptor fields to be used for the automatic exposure control after the display is updated, the operator can set a desired receptor field on the receptor field candidate dialog 1301 again in a similar manner to the above-described processing. At this time, the mark 302 enabling the identification of the orientation of the radiation detector 115 in the receptor field option 1302 is displayed after updated from the display illustrated in FIG. 13A to the state rotated by 90 degrees.

While the button capable of switching on or off the rotation linkage setting has been described above as an example of the rotation linkage setting portion 1303, the rotation linkage setting portion 1303 is not limited thereto. The rotation linkage setting portion 1303 may be configured differently as long as the orientation of the radiation detector 115 is detected and the information about the orientation is reflected in the display of the receptor field display form 506. For example, the rotation linkage setting portion 1303 may be a button serving as a trigger to cause the control unit 211 to request the detection unit of the radiation detector 115 to transmit the information about the orientation, instead of being the button capable of switching on or off the rotation linkage setting. In this case, when the operator presses the button, the control unit 211 requests the detection unit of the radiation detector 115 to transfer the information about the orientation. Then, the information about the orientation is transmitted from the detection unit that has received the request, and the control unit 211 acquires the transmitted information about the orientation of the radiation detector 115 and updates the display of the receptor field display form 506 based on the acquired information about the orientation.

In other words, the rotation linkage setting portion 1303 may be configured to cause the control unit 211 to acquire the information about the orientation of the radiation detector 115 as appropriate and update the display of the receptor field display form 506 based on the acquired information about the orientation. Alternatively, the rotation linkage setting portion 1303 may be configured so that, when the transfer of the information about the orientation is requested based on an operation of the operator, the control unit 211 acquires the information about the orientation of the radiation detector 115 and updates the display of the receptor field display form 506 based on the acquired information about the orientation.

As described above, the receptor field display form 506 can be updated based on the information about the orientation of the radiation detector 115, so that the actual orientation of the radiation detector 115 and the displayed state of the receptor fields 301 can match each other. As a result, in the imaging using the radiation detector 115 having the built-in AEC function, even when the operator selects a plurality of receptor fields to be used for the automatic exposure control from among the receptor fields 301, the operator can easily identify the positions of the selected receptor fields.

The exemplary embodiments of the disclosure can also be implemented by processing that supplies a program for implementing one or more functions according to the above-described exemplary embodiments to a system or an apparatus via a network or a storage medium, and causes one or more processors in a computer of the system or the apparatus to read and execute the program. Alternatively, the exemplary embodiments of the disclosure can also be implemented by a circuit (e.g., an application specific integrated circuit (ASIC)) for implementing one or more functions according to the above-described exemplary embodiments.

The control apparatus 110 according to each of the above-described exemplary embodiments may be implemented as a single apparatus or may be configured in such a manner that a plurality of apparatuses is combined and communicated with each other to perform the above-described processing, and both of the configurations are included in the exemplary embodiments of the disclosure. The above-described processing may be performed by a common server apparatus or a server group. A plurality of apparatuses included in the control apparatus 110 may not necessarily be present in the same facility or the same country as long as the apparatuses are communicable with each other at a predetermined communication rate.

The exemplary embodiments of the disclosure also include an exemplary embodiment in which a program of software for implementing the functions according to the above-described exemplary embodiments is supplied to a system or an apparatus, and a computer of the system or the apparatus reads and executes a code of the supplied program.

Thus, the program code installed on the computer so that the processing according to the exemplary embodiments is implemented by the computer is also one of the exemplary embodiments of the disclosure. An operating system (OS) or the like running on the computer partially or entirely performs the actual processing based on an instruction included in the program read by the computer, and the functions according to the above-described exemplary embodiments can also be implemented by this processing.

Furthermore, the disclosure is not limited to the above-described exemplary embodiments and the above-described exemplary embodiments can be modified in various manners (including organic combinations of the exemplary embodiments) based on the spirit of the disclosure, and such modifications are not excluded from the scope of the disclosure. All possible configurations obtained by combining the above-described exemplary embodiments are also included in exemplary embodiments of the disclosure.

According to the exemplary embodiments of the disclosure, the operator can easily identify the position of a receptor field.

Other Embodiments

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2021-132310, filed Aug. 16, 2021, which is hereby incorporated by reference herein in its entirety.

What is claimed is:

1. An apparatus comprising:
   an acquisition unit configured to acquire information about an orientation of a detector, the detector being configured to capture a radiation image by detecting radiation, the detector including a plurality of receptor fields for performing automatic exposure control and a mark enabling identification of the orientation of the detector; and
   a display control unit configured to display an object related to the detector and being marked on a display unit in a state where the information about the orientation of the detector acquired by the acquisition unit is reflected.

2. The apparatus according to claim 1, further comprising a setting unit configured to set rotation information about the detector,
wherein the acquisition unit acquires the rotation information set by the setting unit, as the information about the orientation of the detector, and
wherein the display control unit displays the object rotated based on the acquired rotation information on the display unit.

3. The apparatus according to claim 2, wherein, in a case where the acquired rotation information is different from a predetermined value, the display control unit updates the display in such that the object displayed on the display unit is rotated based on the acquired rotation information.

4. The apparatus according to claim 3, wherein the acquired rotation information includes a rotation angle of the detector, and a default value of the rotation angle is 0 degrees, and
wherein, in a case where the rotation angle is not set to 0 degrees, the display control unit updates the display in such that the object is rotated by the rotation angle.

5. The apparatus according to claim 2, wherein the display control unit displays a button for receiving update of the rotation information from an operator, on the display unit together with the object.

6. The apparatus according to claim 1, wherein the acquisition unit acquires the information about the orientation of the detector that is detected by a detection unit included in the detector and configured to detect the orientation of the detector, and
wherein the display control unit displays the object on the display unit based on the acquired information about the orientation of the detector.

7. The apparatus according to claim 6, wherein the display control unit displays, on the display unit, a linkage setting portion for setting whether to update the display of the object based on the information about the detected orientation of the detector.

8. The apparatus according to claim 7, wherein the acquisition unit acquires the information about the orientation of the detector from the detector as appropriate in a case where the display of the object is set to be updated based on the information about the orientation of the detector, on the linkage setting portion, and
wherein the display control unit updates the display of the object based on the acquired information about the orientation of the detector.

9. The apparatus according to claim 7, wherein the acquisition unit requests the detector to transfer the information about the orientation in a case where an instruction for updating the display of the object based on the information about the orientation of the detector is issued on the linkage setting portion, and
wherein the display control unit updates the display of the object based on the information about the orientation of the detector that is transmitted in response to the request of the acquisition unit.

10. The apparatus according to claim 1, wherein the display control unit displays, on the display unit, a receptor field setting screen for setting a receptor field to be used for the automatic exposure control from among the plurality of receptor fields.

11. The apparatus according to claim 10, wherein the display control unit displays, on the display unit, the receptor field setting screen for enabling the operator to manually set the receptor field to be used from among the plurality of receptor fields.

12. The apparatus according to claim 10, wherein the display control unit displays, on the display unit, the receptor field setting screen for setting the receptor field to be used from among a plurality of predetermined combinations of the plurality of receptor fields.

13. The apparatus according to claim 12, wherein the display control unit displays, on the display unit, the plurality of predetermined combinations that is different for each imaging part.

14. The apparatus according to claim 13, further comprising a combination setting unit configured to set the plurality of predetermined combinations for each imaging part,
wherein the display control unit displays, on the display unit, the plurality of predetermined combinations set for each imaging part.

15. A control apparatus comprising:
an acquisition unit configured to acquire information about an orientation of a detector, the detector being configured to capture a radiation image by detecting radiation, the detector including a mark located near a side that defines an outer edge of the detector and enabling identification of the orientation of the detector and a plurality of receptor fields located in such a way that distances of the plurality of receptor fields from the side are different from each other and for performing automatic exposure control; and
a display control unit configured to display a candidate for a receptor field to be used for performing the automatic exposure control among the plurality of receptor fields on a display unit,
wherein the display control unit displays the candidate for a receptor field to be used for performing the automatic exposure control based on the information about the orientation of the detector acquired by the acquisition unit.

16. The control apparatus according to claim 15, wherein the acquisition unit acquires information about the orientation of the detector detected by a detection unit configured to detect the orientation of the detector and included in the detector.

17. A system comprising:
a detector configured to capture a radiation image by detecting radiation, and including a plurality of receptor fields for performing automatic exposure control and a mark enabling identification of an orientation of the detector; and
an apparatus configured to communicate with the detector to receive the radiation image and perform operation control,
wherein the detector includes a detection unit configured to detect the orientation of the detector, and
wherein the apparatus includes:
an acquisition unit configured to acquire information about the detected orientation of the detector, and
a display control unit configured to display an object related to the detector and being marked on a display unit in a state where the information about the orientation of the detector acquired by the acquisition unit is reflected.

18. A system comprising:
an imaging apparatus including a generation unit configured to perform irradiation with radiation, and a detector configured to capture a radiation image by detecting the radiation and including a plurality of receptor fields for performing automatic exposure control and a mark enabling identification of an orientation of the detector; and an apparatus configured to communicate with the imaging apparatus to receive the radiation image and perform operation control, wherein the imaging apparatus includes an imaging unit configured to capture an image of the detector, and wherein the apparatus includes:

an acquisition unit configured to acquire the captured image of the detector, a determination unit configured to determine the orientation of the detector based on the acquired image of the detector, and a display control unit configured to display an object related to the detector and being marked on a display unit in a state where the orientation of the detector determined by the determination unit is reflected.

19. A method comprising:

acquiring information about an orientation of a detector, the detector being configured to capture a radiation image by detecting radiation, the detector including a plurality of receptor fields for performing automatic exposure control and a mark enabling identification of the orientation of the detector; and displaying an object related to the detector and being marked on a display unit in a state where the information about the orientation of the detector acquired in the acquiring is reflected.

20. A non-transitory computer-readable storage medium storing a program for causing a computer to execute a method, the method comprising:

acquiring information about an orientation of a detector, the detector being configured to capture a radiation image by detecting radiation, the detector including a plurality of receptor fields for performing automatic exposure control and a mark enabling identification of the orientation of the detector; and displaying an object related to the detector and being marked on a display unit in a state where the information about the orientation of the detector acquired in the acquiring is reflected.

21. A radiation imaging system comprising:

a detector configured to capture a radiation image by detecting radiation and including a mark located near a side that defines an outer edge of the detector and enabling identification of the orientation of the detector, a plurality of receptor fields located in such a way that distances of the plurality of receptor fields from the side are different from each other and for performing automatic exposure control, and a detection unit configured to detect an orientation of the detector; and a control apparatus configured to communicate with the detector to receive the radiation image and perform operation control, wherein the control apparatus includes;

an acquisition unit configured to acquire information about the orientation of the detector detected by the detection unit; and a display control unit configured to display a candidate for a receptor field to be used for performing the automatic exposure control among the plurality of receptor fields on a display unit based on the information about the orientation of the detector acquired by the acquisition unit.

22. A method comprising:

acquiring information about an orientation of a detector, the detector being configured to capture a radiation image by detecting radiation, the detector including a mark located near a side that defines an outer edge of the detector and enabling identification of the orientation of the detector and a plurality of receptor fields located in such a way that distances of the plurality of receptor fields from the side are different from each other and for performing automatic exposure control; and displaying a candidate for a receptor field to be used for performing the automatic exposure control among the plurality of receptor fields on a display unit based on the information about the orientation of the detector acquired in the acquiring.

23. A non-transitory computer-readable storage medium storing a program for causing a computer to execute a method, the method comprising:

acquiring information about an orientation of a detector, the detector being configured to capture a radiation image by detecting radiation, the detector including a mark located near a side that defines an outer edge of the detector and enabling identification of the orientation of the detector and a plurality of receptor fields located in such a way that distances of the plurality of receptor fields from the side are different from each other and for performing automatic exposure control; and displaying a candidate for a receptor field to be used for performing the automatic exposure control among the plurality of receptor fields on a display unit based on the information about the orientation of the detector acquired in the acquiring.

* * * * *